(12) United States Patent
Rosen et al.

(10) Patent No.: US 11,298,335 B2
(45) Date of Patent: Apr. 12, 2022

(54) ARSINOTHRICIN AND METHODS OF TREATING INFECTIONS USING ARSINOTHRICIN

(71) Applicants: Barry Philip Rosen, Coral Gables, FL (US); Masafumi Yoshinaga, Miami, FL (US)

(72) Inventors: Barry Philip Rosen, Coral Gables, FL (US); Masafumi Yoshinaga, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 11 days.

(21) Appl. No.: 16/163,055

(22) Filed: Oct. 17, 2018

(65) Prior Publication Data
US 2020/0121632 A1    Apr. 23, 2020

(51) Int. Cl.
*A61K 31/285*    (2006.01)
*A61P 31/04*    (2006.01)
*C12N 9/10*    (2006.01)

(52) U.S. Cl.
CPC ............ *A61K 31/285* (2013.01); *A61P 31/04* (2018.01); *C12N 9/1029* (2013.01); *C12Y 203/01183* (2013.01)

(58) Field of Classification Search
CPC ............................... A61K 31/285; A61P 31/04
See application file for complete search history.

(56) References Cited

U.S. PATENT DOCUMENTS

2004/0157802 A1*   8/2004   Horowitz et al.

OTHER PUBLICATIONS

Kuramata et al. (Environ. Chem. 2016, 13, 723-731/.*
Brian Thomas, Ph. D. ("Arsenic-Eating Bacteria: A New Frontier in Life Science?" https://www.icr.org/article/arsenic-eating-bacteria-new-frontier. (Dec. 14, 2010)). (Year: 2010).*
Harth, G. et al., "An Inhibitor of Exported *Mycobacterium tuberculosis* Glutamine Synthetase Selectively Blocks the Growth of Pathogenic Mycobacteria in Axenic Culture and in Human Monocytes: Extracellular Proteins as Potential Novel Drug Targets." J. Exp. Med., May 3, 1999, 189(9): 1425-1435.
Harth, G. et al., "Inhibition of *Mycobacterium tuberculosis* Glutamine Synthetase as a Novel Antibiotic Strategy against Tuberculosis: Demonstration of Efficacy In Vivo." Infection and Immunity, Jan. 2003, 71(1): 456-464.
Kritharis, A. et al., "The evolving use of arsenic in pharmacotherapy of malignant disease." Ann Hematol, 2013, 92: 719-730.
Kuramata, M. et al., "Arsinothricin, a novel organoarsenic species produced by a rice rhizosphere bacterium." Environ. Chem., 2016, 13: 723-731.
Mowbray, S.L. et al., "Inhibition of Glutamine Synthetase: A Potential Drug Target in *Mycobacterium tuberculosis*." Molecules, 2014, 19: 13161-13176.
Paez-Espino, A.D. et al., "The two paralogue phoN (phosphinothricin acetyl transferase) genes of Pseudomonas putida encode functionally different proteins." Environmental Microbiology, 2015, 17(9): 3330-3340.
Nadar, V.S., et al., "Arsinothricin, an arsenic-containing non-proteinogenic amino acid analog of glutamate, is a broad-spectrum antibiotic." Communications Biology, 2019, 2(1): 1-12.

* cited by examiner

*Primary Examiner* — Jeffrey S Lundgren
*Assistant Examiner* — Chris E Simmons
(74) *Attorney, Agent, or Firm* — Saliwanchik, Lloyd & Eisenschenk

(57) ABSTRACT

Certain embodiments of the invention pertain to a method of treating an infection in a subject caused by an infectious agent other than *Escherichia coli*, the method comprising administering to the subject arsinothricin or a salt thereof. The infectious agent other than *E. coli* can be a bacterium, protozoan, helminth, archaebacterium, or a fungus. In preferred embodiments, the infectious agent is *Mycobacterium tuberculosis*, *Mycobacterium bovis*, or *Enterobacter cloacae*. The invention also pertains to a method of treating an infection in a subject caused by an infectious agent, comprising administering to the subject arsinothricin or a salt thereof in combination with an inhibitor of phosphinothricin N-acetyltransferase or arsinothricin N-acetyltransferase. In certain such embodiments, the infectious agent expresses phosphinothricin N-acetyltransferase or arsinothricin N-acetyltransferase. Further embodiments provide compositions comprising arsinothricin or a salt thereof and an inhibitor of phosphinothricin N-acetyltransferase or arsinothricin N-acetyltransferase.

14 Claims, 17 Drawing Sheets
(10 of 17 Drawing Sheet(s) Filed in Color)
Specification includes a Sequence Listing.

FIG. 1A: AST 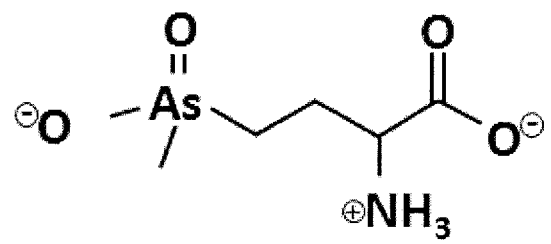
FIG. 1B: PT 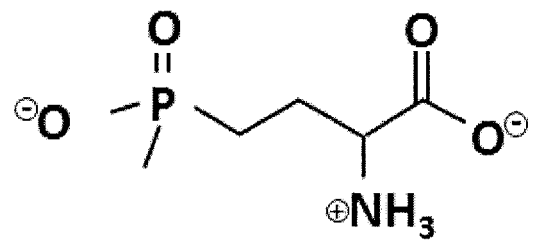
FIG. 1C: Glutamate 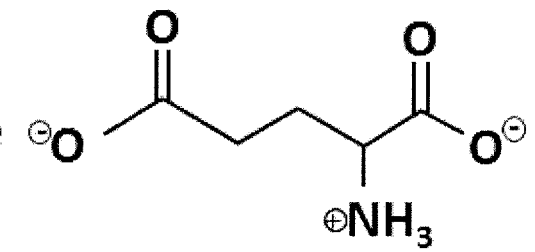
FIG. 1D: MSO 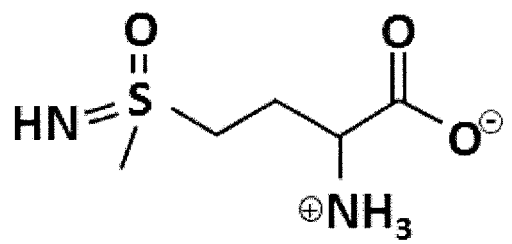

A: AST　　　　B: L-PT　　　　C: L-MSO

```
PpArsN1    ---MHSGIDIRVARPEDAEEIQIIYAPIVLNTAISFEEAVPSVEQMRERISTTLQTYPYL    57
ShPAT      MSPERRPADIRRATEADMPAVCTIVNHYIETSTVNFRTEPQEPQEWTDDLVRLRERYPWL    60
            :  *** *   *   :  *    :,::;,*,    ,  ::  : :   : **:*

PpArsN1    VAVREGRVVGYAYASQHRARAAYRWAVDVTVYVAEGQRRSGIARQLYDVLLPVLKRLGYR    117
ShPAT      VAEVDGEVAGIAYAGPWKARNAYDWTAESTVYVSPRHQRTGLGSTLYTHLLKSLEAQGFK    120
           **  :*,*,* ***,  :** ** *:,: ****:   ::*:*:,  ** **  *:  *::

PpArsN1    SAYAGIALPNEGSVGLHERLGFQHIGTFPQVGFKLDAWHDVGYWRFDFGDEGLHPEAPLG    177
ShPAT      SVVAVIGLPNDPSVRMHEALGYAPRGMLRAAGFKHGNWHDVGFWQLDFSLPVP--PRPVL    178
           *, * *,***: **  :** **:    * :  ,***  , *****:*:,**,      *:

PpArsN1    FLSQIPVPR    186
ShPAT      PVTEI----    183
            :::*
```

FIG. 13

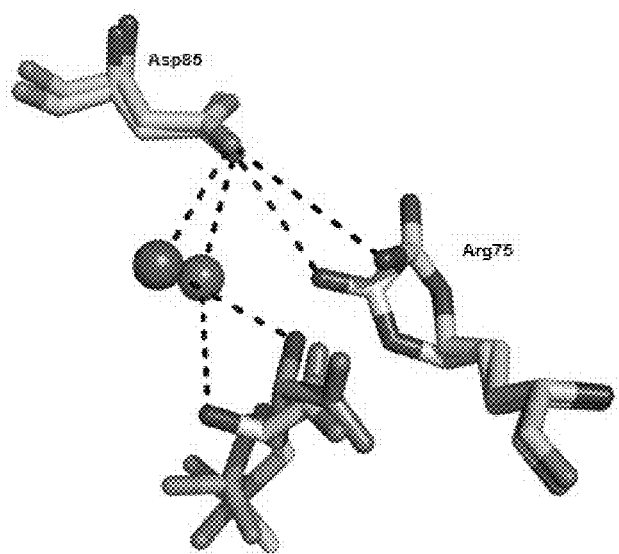

FIG. 14

SEQUENCE LISTING

<160> NUMBER OF SEQ ID NOS: 4

<210> SEQ ID NO 1
<211> LENGTH: 29
<212> TYPE: DNA
<213> ORGANISM: Artificial sequence
<220> FEATURE:
<223> OTHER INFORMATION: primer

<400> SEQUENCE: 1
ccagccatgg atagcggaat cgatattcg                              29

<210> SEQ ID NO 2
<211> LENGTH: 29
<212> TYPE: DNA
<213> ORGANISM: Artificial sequence
<220> FEATURE:
<223> OTHER INFORMATION: primer

<400> SEQUENCE: 2
ccagaagctt acgaggcact gggatttgg                              29

<210> SEQ ID NO 3
<211> LENGTH: 186
<212> TYPE: PRT
<213> ORGANISM: Pseudomonas spp.

<400> SEQUENCE: 3

Met His Ser Gly Ile Asp Ile Arg Val Ala Arg Pro Glu Asp Ala Glu
1               5                   10                  15

Glu Ile Gln Ile Ile Tyr Ala Pro Ile Val Leu Asn Thr Ala Ile Ser
                20                  25                  30

Phe Glu Glu Ala Val Pro Ser Val Gln Met Arg Glu Arg Ile Ser
            35                  40                  45

Thr Thr Leu Gln Thr Tyr Pro Tyr Leu Val Ala Val Arg Glu Gly Arg
        50                  55                  60

Val Val Gly Tyr Ala Tyr Ala Ser Gln His Arg Ala Arg Ala Ala Tyr
65                  70                  75                  80

Arg Trp Ala Val Asp Val Thr Val Tyr Val Ala Glu Gly Gln Arg Arg
                85                  90                  95

```
Ser Gly Ile Ala Arg Gln Leu Tyr Asp Val Leu Leu Pro Val Leu Lys
            100                 105                 110

Arg Leu Gly Tyr Arg Ser Ala Tyr Ala Gly Ile Ala Leu Pro Asn Glu
            115                 120                 125

Gly Ser Val Gly Leu His Glu Arg Leu Gly Phe Gln His Ile Gly Thr
            130                 135                 140

Phe Pro Gln Val Gly Phe Lys Leu Asp Ala Trp His Asp Val Gly Tyr
145                 150                 155                 160

Trp Arg Phe Asp Phe Gly Asp Glu Gly Leu His Pro Glu Ala Pro Leu
                165                 170                 175

Gly Phe Leu Ser Gln Ile Pro Val Pro Arg
            180                 185

<210> SEQ ID NO 4
<211> LENGTH: 183
<212> TYPE: PRT
<213> ORGANISM: Streptomyces hygroscopicus

<400> SEQUENCE: 4

Met Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
            20                  25                  30

Thr Val Asn Phe Arg Thr Glu Pro Gln Glu Pro Gln Glu Trp Thr Asp
            35                  40                  45

Asp Leu Val Arg Leu Arg Glu Arg Tyr Pro Trp Leu Val Ala Glu Val
        50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
            115                 120                 125

Pro Asn Asp Pro Ser Val Arg Met His Glu Ala Leu Gly Tyr Ala Pro
            130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
            180
```

ARSINOTHRICIN AND METHODS OF TREATING INFECTIONS USING ARSINOTHRICIN

GOVERNMENT SUPPORT

This invention was made with government support under Grant No. GM055425 awarded by National Institutes of Health. The government has certain rights in the invention.

The Sequence Listing for this application is labeled "SeqList-16Oct18-ST25," which was created on Oct. 16, 2018, and is 4 KB. The Sequence Listing is incorporated herein by reference in its entirety.

BACKGROUND OF THE INVENTION

New antibiotics are urgently needed because the emergence of resistance has rendered many clinically used antibiotics ineffective. Human tuberculosis (TB), the top global infectious disease killer caused by *Mycobacterium tuberculosis* (MTB), is becoming more difficult to treat due to the drug resistance. The World Health Organization (WHO) declared multidrug-resistant (MDR) TB a global public health crisis, calling a pressing need for development of new and innovative antibiotics. In addition to MTB, the WHO recently issued a global priority pathogen list of antibiotic resistant bacteria that pose the greatest threat to human health to guide and promote research and development of new antibiotics (see world-wide-website: who.int/en/newsroom/detail/27-02-2017-who-publishes-list-of-bacteria-for-which-new-antibiotics-are-urgently-needed).

The use of arsenicals as antimicrobial and anticancer agents is well-established. The first synthetic antimicrobial agents were the organoarsenicals atoxyl (p-aminophenylarsenate, also known as p-arsanilic acid) and salvarsan (arsphenamine). While salvarsan is no longer in clinical use, the organoarsenical melarsoprol, developed in 1949, is still recommended by the WHO for treatment of second-stage *Trypanosoma brucei* sleeping sickness. The aromatic arsenicals atoxyl, roxarsone (4-hydroxy-3-nitrophenylarsenate) and nitarsone (4-nitrophenylarsenate) are used world-wide as antimicrobials for the prevention of *Coccidioides* and *Histomonas* infections in poultry. Arsenic trioxide is currently the treatment of choice for all-trans retinoic acid unresponsive acute promyelocytic anemia.

BRIEF SUMMARY OF THE INVENTION

Certain embodiments of the invention provide a method of treating an infection in a subject caused by an infectious agent other than *Escherichia coli*, comprising administering to the subject arsinothricin or a salt thereof. The infectious agent other than *E. coli* can be a bacterium, protozoan, helminth, archaebacterium, or a fungus. A bacterium can be, for example, *Burkolderia* spp., *Sinorhizobium* spp., *Schewanella* spp., *Bacillus* spp., *Corynebacterium* spp., *Mycobacterium* spp., or *Enterobacter* spp. Preferably, the bacterium is *Mycobacterium bovis, Mycobacterium tuberculosis*, carbapenem-resistant *Acinetobacter baumannii*, carbapenem-resistant *Pseudomonas aeruginosa*, carbapenem-resistant Enterobacteriaceae, vancomycin-resistant *Enterococcus faecium*, methicillin- and/or vancomycin-resistant *Staphylococcus aureus*, clarithromycin-resistant *Helicobacter pylori*, fluoroquinolone-resistant *Campylobacter* spp., fluoroquinolone-resistant Salmonellae, cephalosporin and/or fluoroquinolone-resistant *Neisseria gonorrhoeae*, penicillin-non-susceptible *Streptococcus pneumoniae*, ampicillin-resistant *Haemophilus influenzae*, fluoroquinolone-resistant *Shigella* spp., or carbapenem-resistant *Enterobacter cloacae*. In preferred embodiments, the infectious agent is *Mycobacterium tuberculosis, Mycobacterium bovis*, or carbapenem-resistant *Enterobacter cloacae*.

In certain embodiments, the infectious agent expresses phosphinothricin N-acetyltransferase or arsinothricin N-acetyltransferase, and the method further comprises administering to the subject an inhibitor of phosphinothricin N-acetyltransferase or arsinothricin N-acetyltransferase.

Further embodiments of the invention provide a method of treating an infection in a subject caused by an infectious agent, comprising administering to the subject arsinothricin or a salt thereof in combination with an inhibitor of phosphinothricin N-acetyltransferase or arsinothricin N-acetyltransferase. The infectious agent can be a bacterium, protozoan, helminth, archaebacterium, or a fungus. A bacterium can be, for example, *Escherichia* spp., *Burkolderia* spp., *Sinorhizobium* spp., *Schewanella* spp., *Bacillus* spp., *Corynebacterium* spp., *Mycobacterium* spp., or *Enterobacter* spp. Preferably, the bacterium is a priority pathogen identified by the World Health Organization such as *Mycobacterium bovis, Mycobacterium tuberculosis*, carbapenem-resistant *Acinetobacter baumannii*, carbapenem-resistant *Pseudomonas aeruginosa*, carbapenem-resistant Enterobacteriaceae, vancomycin-resistant *Enterococcus faecium*, methicillin- and/or vancomycin-resistant *Staphylococcus aureus*, clarithromycin-resistant *Helicobacter pylori*, fluoroquinolone-resistant *Campylobacter* spp., fluoroquinolone-resistant Salmonellae, cephalosporin and/or fluoroquinolone-resistant *Neisseria gonorrhoeae*, penicillin-non-susceptible *Streptococcus pneumoniae*, ampicillin-resistant *Haemophilus influenzae*, fluoroquinolone-resistant *Shigella* spp or carbapenem-resistant *Enterobacter cloacae*. In preferred embodiments, the infectious agent expresses phosphinothricin N-acetyltransferase or arsinothricin N-acetyltransferase.

Even further embodiments of the invention provide compositions comprising arsinothricin or a salt thereof in combination with an inhibitor of phosphinothricin N-acetyltransferase or arsinothricin N-acetyltransferase.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D. Chemical structure of glutamate and analogs. A. Arsinothricin (AST); B. phosphinothricin (PT); C. glutamate; D. methionine sulfoximine (MSO).

Figure 2A:
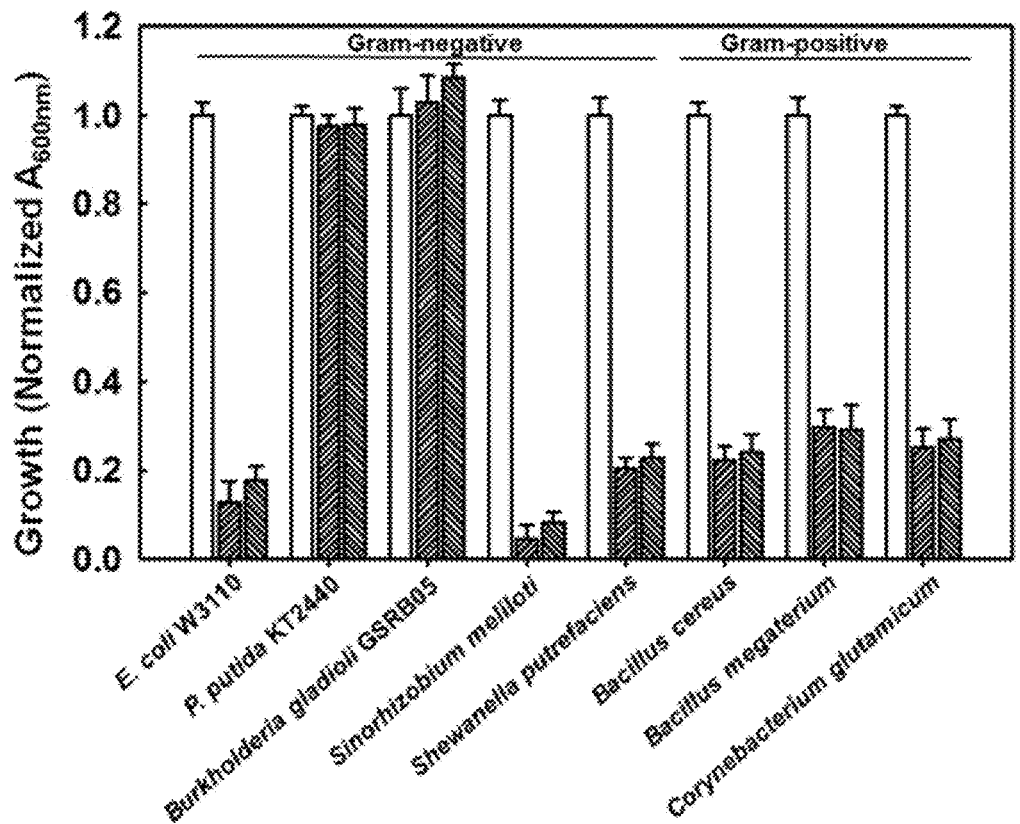
FIGS. 2A-2E. AST is a broad-spectrum antibiotic. A: AST inhibits growth of both Gram-negative and Gram-positive bacteria. Strains were cultured in M9 medium in the absence (left) or presence of 25 µM AST (middle) or 800 µM D,L-PT (right) as described in and growth estimated from the $A_{600}$ nm after 24 h. B: Pentavalent AST is more toxic than trivalent As(III). The toxicity of AST (V) was compared with MAs(III) (□) and As(III) (○) in *E. coli* AW3110 grown in M9 medium. Growth was estimated from $A_{600\ nm}$ after 24 h. Data are the mean±SE (n=3). C: Effect of AST on mycobacterial growth. Cultures of *M. bovis* BCG at an initial density of $10^5$ cells/ml were incubated at 37° C. in a 5% $CO_2$ atmosphere for up to 4 weeks in the presence or absence of indicated concentrations of GS inhibitors L-MSO, D,L-PT or AST. Growth was estimated from $A_{600\ nm}$. Data are the mean±SE (n=3). D: Effect of AST on carbapenem-resistant

*E. cloacae*. Cells were cultured in M9 medium in the absence (Control) or presence of 25 μM AST, 50 μM D,L-PT or 25 μM MSO and growth estimated from the $A_{600\,nm}$ after 24 h. E: Cytotoxicity of AST in human monocytes. THP-1 cells were incubated in the presence or absence of indicated concentrations of As(III) (○) or AST (▽) for 24 h and the viability was determined by MTT assay as described in Materials and Methods. Data are the mean±SE (n=4).

FIGS. 3A-3D. Prevalence and phylogenetic analysis of arsN1 genes. A: Composition of bacterial arsenic resistance (ars) operons with arsN1 genes. Shown are representative ars operons containing arsN1 (black fill). GenBank accession numbers are given in Materials and Methods. B: Phylogeny of genes for resistance to AST, PT and MSO. The neighbor-joining phylogenetic tree shows the evolutionary relationships of ArsN1 with members from other kingdoms. All arsN1 genes are located in ars operon. PAT: phosphinothricin N-acetyltransferase, MAT: methionine sulfoximine N-acetyltransferase, GenBank accession numbers of bacterial genomes are given in Materials and Methods. C: PpArsN1 confers resistance to PT. Strains: wild type *P. putida* (○); Δars1,2 (▽); *E. coli* AW3110 bearing control plasmid (□) or plasmid carrying PparsN1 (◇). Cells were cultured in M9 medium with the indicated concentrations of D,L-PT. Growth was estimated from $A_{600\,nm}$ after 24 h. D: PpArsN1 confers resistance to AST. Cells were treated with the indicated concentrations of AST as in C.

FIGS. 4A-4F. Structure of PpArsN1. A: Cartoon representation of overall fold of apo-PpArsN1. α helices are shown in green. Helices α1, α2 and α3, α4 are in the outer layers, and the seven β strands are in the inner layer of the sandwich. There is a structurally-conserved β bulge in the middle of the strands. B: Interaction of AST with PpArsN1. The AST binding site is formed by residues from both chains. Arg75, Ala76 and Arg77 (cyan) of chain A project into the AST binding site of chain B, Ile31, Phe33, Ala124 and Val158 (green). Distances between polar atoms are less than 4.0 Å (dotted lines). The methyl group of AST is surrounded by hydrophobic residues Phe33, Ala124 and Val158. C: Interaction of PT-1 (conformation 1) with PpArsN1. The methyl group of PT AST is surrounded by hydrophobic residues Ala124 and Val158. Atoms OEA and OEB of PT make interaction with Arg77 and backbone of Ile31, backbone of Phe33 respectively. D: Interaction of PT-2 (conformation 2) with PpArsN1. The methyl group of PT AST is surrounded by hydrophobic residues Phe33, Ala124 and Val158. Atoms OEA and OEB of PT make interaction with Arg77, backbone of Phe33 and Tyr80 and Arg75 respectively. E: A conformational change of PpArsN1 resulting from ligand binding. A portion of the AST binding site in PpArsN1-AST (green) is superimposed with that of the apo structure (yellow). Left and right cartoons depict chain A and chain B, respectively. Arg77 in chain A and Arg75 in chain B move toward AST when substrate is bound. F: Orientation of AST and PT. When As atom of AST and P atoms of PT-1 and PT-2 are superimposed, carboxylates of PT-2 and AST are oriented 113° relative to each other and carboxylates of PT-1 and AST are oriented same direction.

Figure 5:
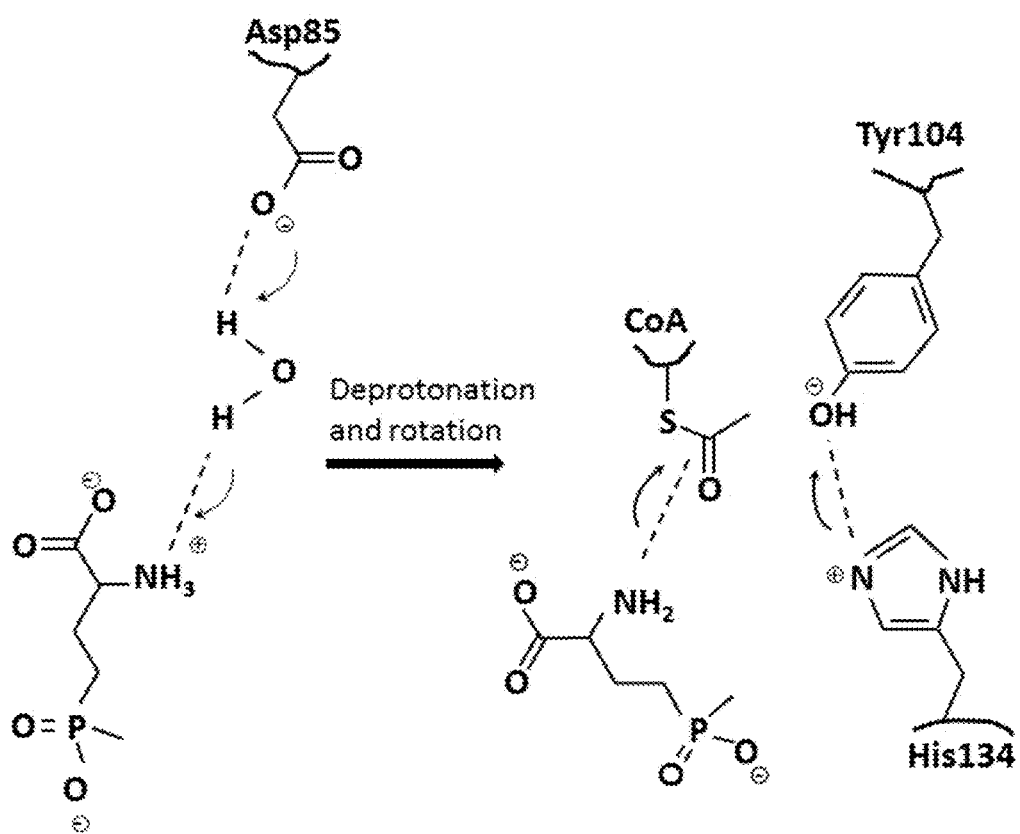

FIG. 5. Proposed catalytic mechanism of PpArsN1. In step 1, the substrate such as AST or PT bind the enzyme in deprotonating mode and the amino group of substrate faces towards the Asp85. The N atom of substrate is then deprotonated by Asp85 as a general base through water molecule as the proton carrier (left). Then deprotonated substrate rotates or rolls towards the catalytic site and the carbonyl of ACoA undergoes to nucleophilic attack by the deprotonated amino group. The oxyanion hole formed by positively charged His134 and its proton donor Tyr104.

Figure 6A:
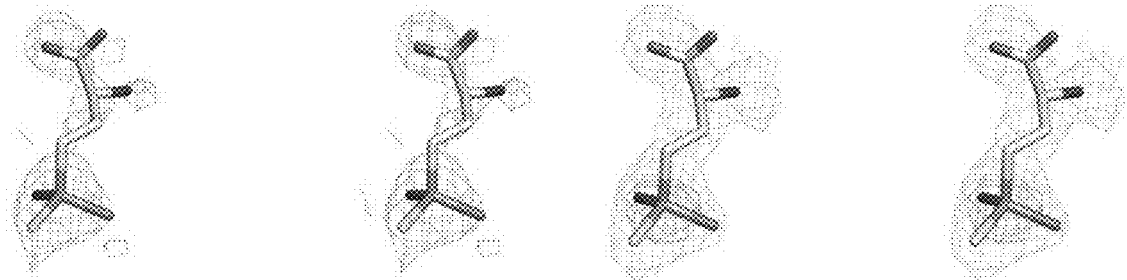
Figure 6B:
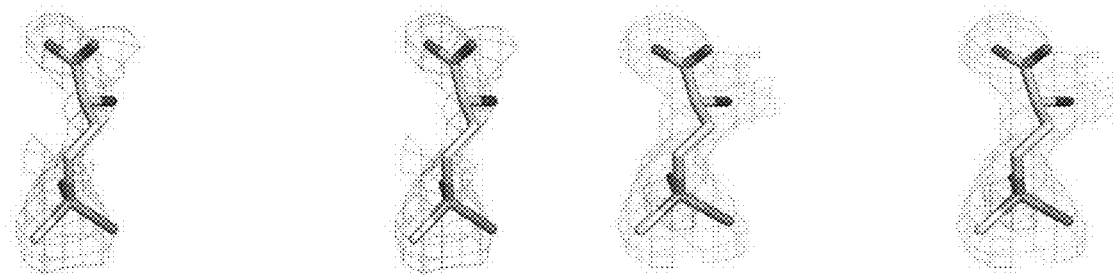

FIGS. 6A-6B. Stereo view of electron density of AST in the ArsN structure. A. AST in chain A. B. AST in chain B. Electron density (2Fo-Fc) map for AST contoured at the 1.0 σ level (gray), omit map (Fo-Fc) at 2.0 σ (green) and anomalous difference map at the 3.0 σ level (red) of AST.

Figure 7A:
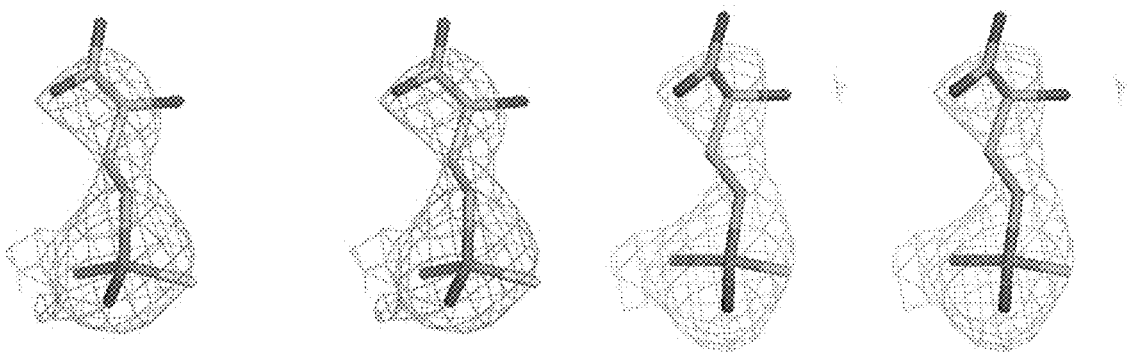
Figure 7B:
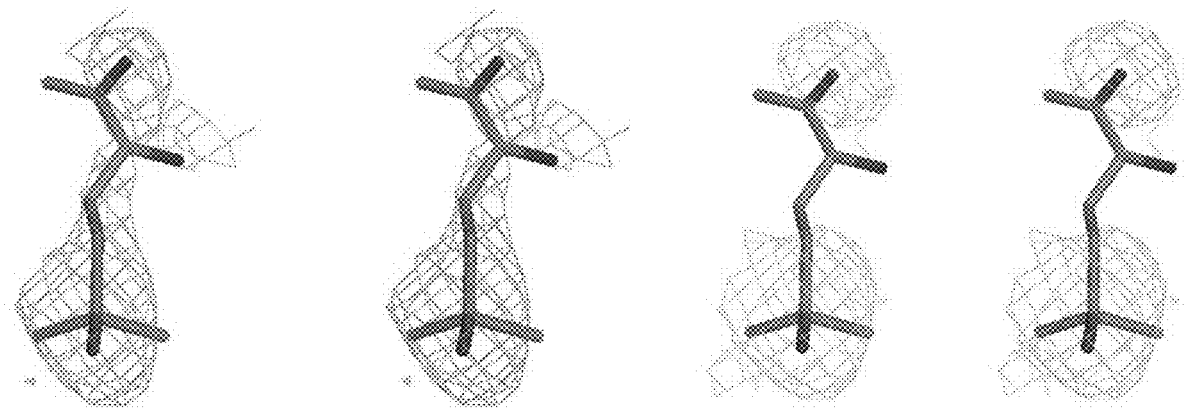

FIGS. 7A-7B. Stereo view of electron density of PT in the PpArsN1 structure. A. PT-2 (confirmation 2). B. PT-1 (confirmation 1). Electron density (2Fo-Fc) map for PT contoured at the 1.0 σ level (gray); Omit map (Fo-Fc) at 2.0 σ level of PT (green).

Figure 8:
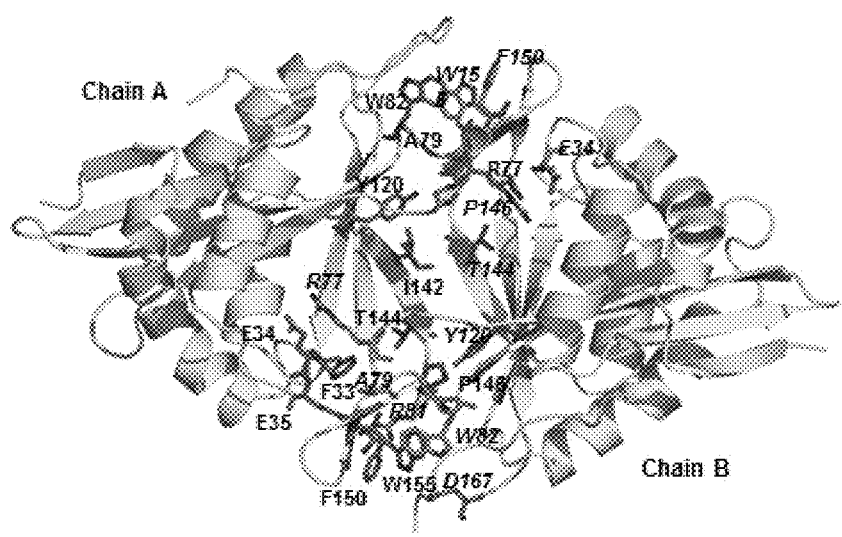

FIG. 8. Crystallographic analysis of the PpArsN1 dimer. The crystallographic asymmetric unit with Chains A and B is shown. The interfacial residues are shown in stick representation. Chain A residues are colored in green, and Chain B residues are shown in brown and are labeled in italics.

Figure 9:
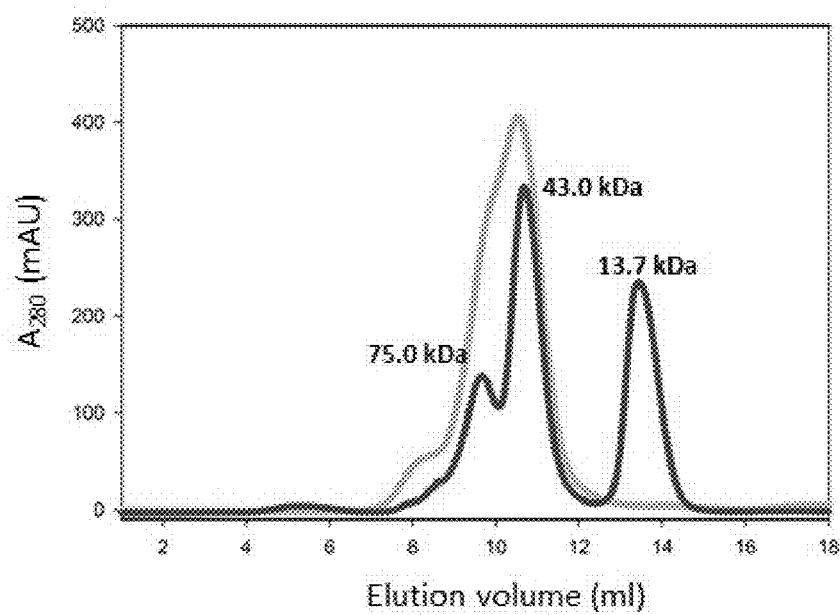

FIG. 9. PpArsN1 is a dimer in solution. Purified protein was chromatographed with Superdex75 using a 10/300 GL column. Elution of PpArsN1 is shown in cyan, and a mixture of proteins of known molecular mass is shown in green.

Figure 10:
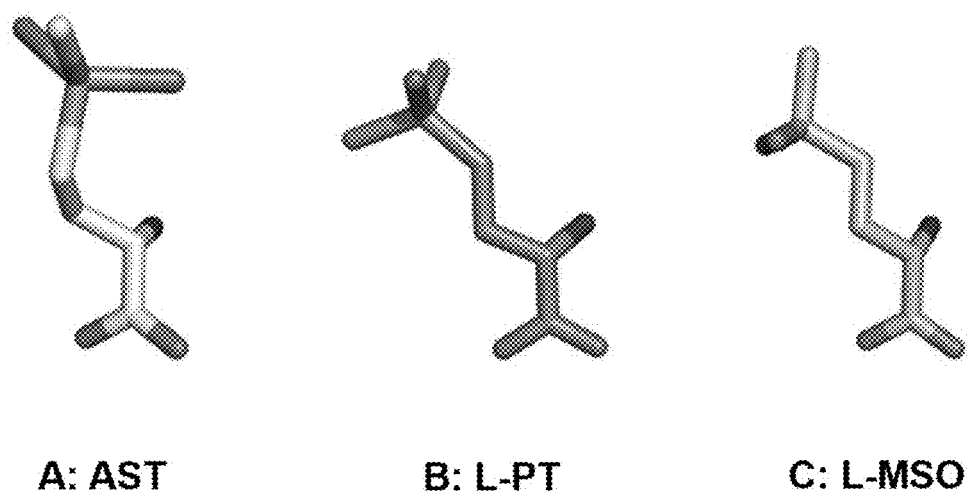

FIG. 10. AST is the L-enantiomer. Comparison of PpArsN1-bound AST (A) with protein-bound L-PT (B) (PDB ID: 1FPY) and L-MSO (C) (PDB ID: 2D3B) available in Protein Data Bank confirms that AST is also in L-form.

Figure 11:
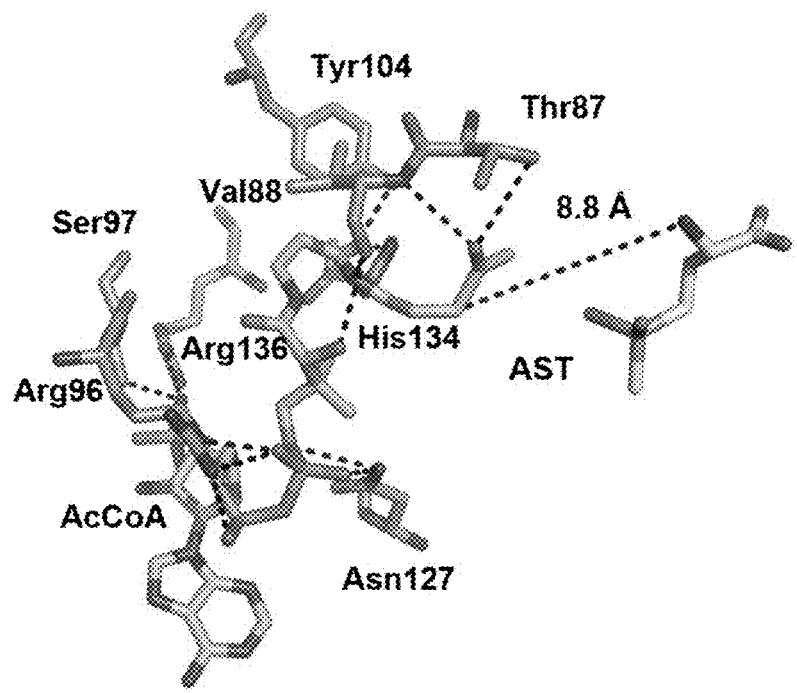

FIG. 11. Model of the acetyl-CoA binding site of PpArsN1. The AcCoA binding site was predicted by docking AcCoA with the structure of PpArsN1 using Autodock4. The dotted lines represent distances of less than 4.0 Å between polar atoms of AcCoA and amino acid residues of the protein. The distance between the amino group of AST and the sulfur atom of AcCoA is 8.8 Å, which is too far for N-acetylation. The substrates are moved into position for N-acetylation by likely conformational changes during the catalytic cycle.

Figure 12:
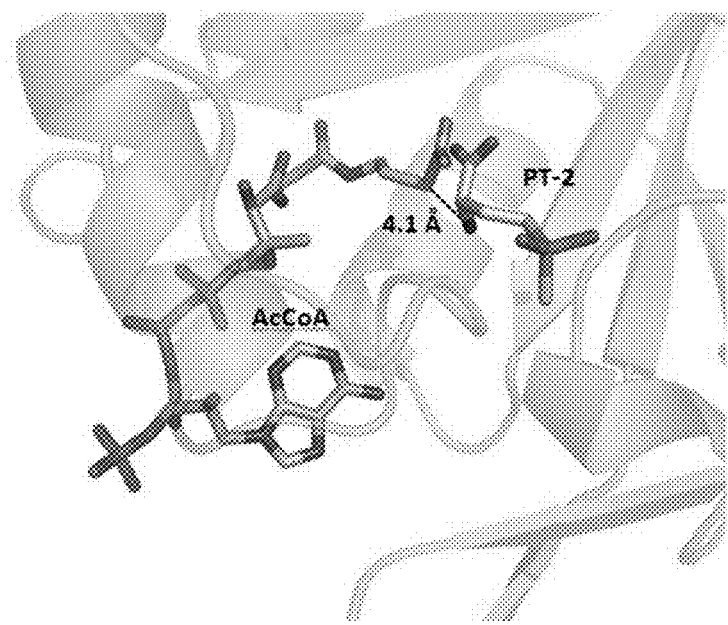

FIG. 12. Model of the acetyl-CoA binding site of PT-bound PpArsN1 in the PT-2 conformation. The distance between the amino group of PT-2 and the sulfur atom of AcCoA is 4.1 Å, which is within the possible distance for N-acetylation.

FIG. 13. Protein sequence alignment of PpArsN1 (SEQ ID NO: 3) and ShPAT (SEQ ID NO: 4). A conserved catalytic Glu88 acts as a general base from ShPAT and the corresponding residue in PpArsN1 (Asp85) are highlighted in yellow.

FIG. 14. Superposition of AST (white) and PT-1 (blue). The amino group of AST and PT interacts Asp85 through water molecules. The residues from PpArsN1-AST and PpArsN1-PT are shown in tan and green, respectively. The water molecules are in blue sphere.

Figure 15:
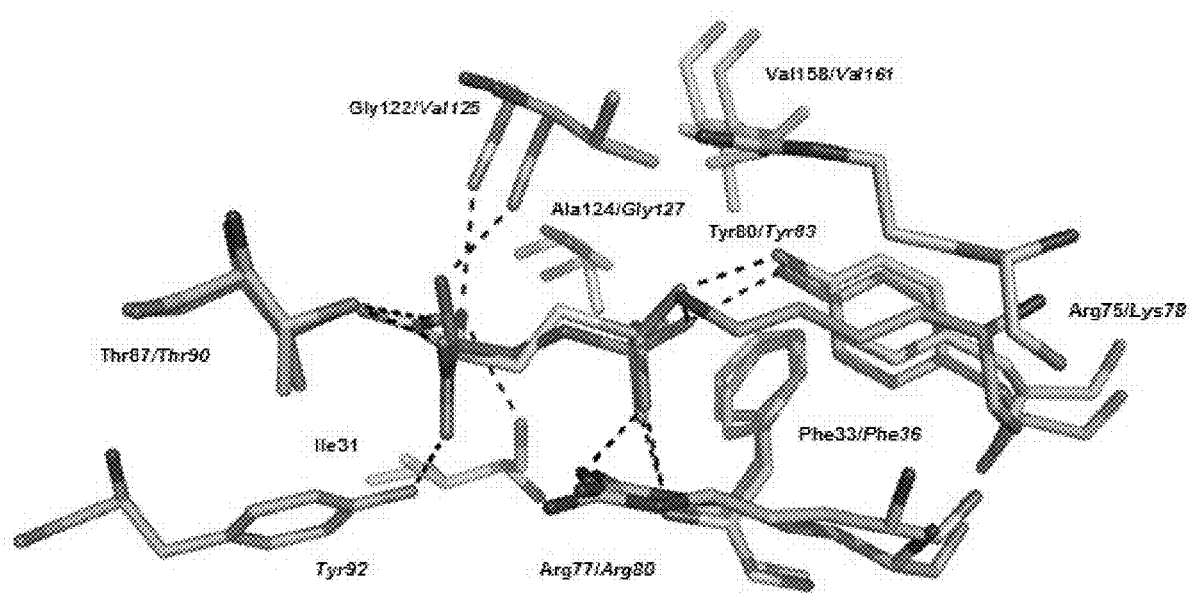

FIG. 15. Superposition of the substrate binding site of BAR (cyan) and PpArsN1-PT-2 (green). The position of the phosphorus atom of PT (purple) and PT-2 (tan) coincide with each other and the carboxylate groups of each substrate are oriented in same directions. Residues of ShPAT are labeled in italics.

Figure 16:
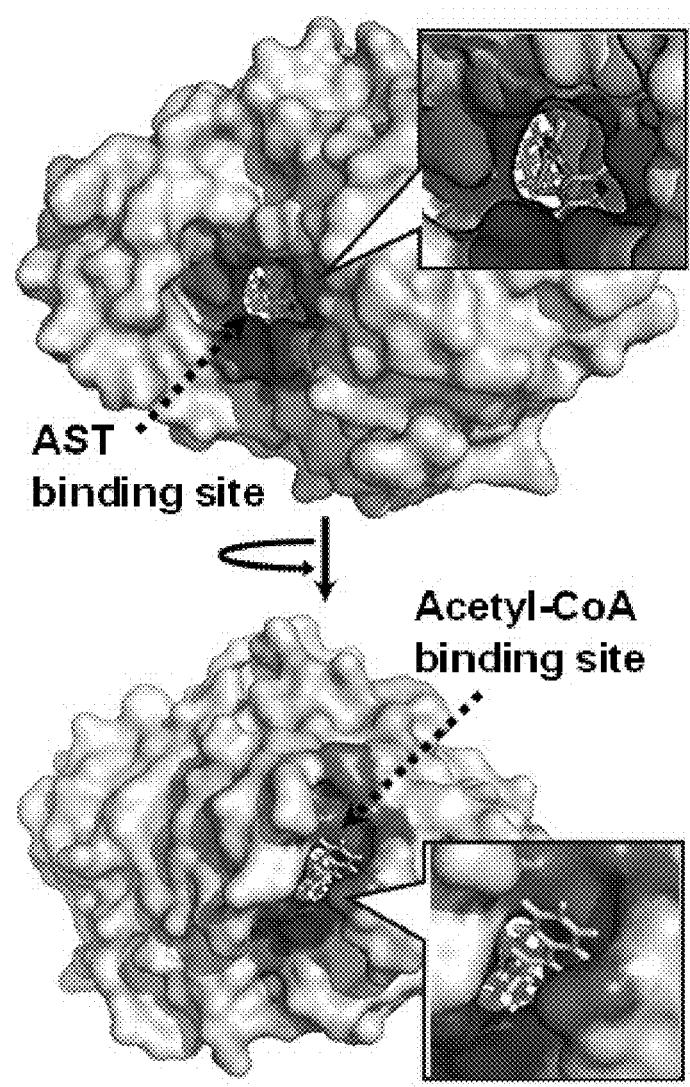

FIG. 16. The PpArsN1 cavity used for identification of in silico inhibitors.

DETAILED DISCLOSURE OF THE INVENTION

The emergence and spread of bacterial resistance highlights the urgent need for new antibiotics. Organoarsenicals have been used as antimicrobials since Paul Ehrlich's discovery of salvarsan. Recently a soil bacterium was shown to produce the organoarsenical arsinothricin. This disclosure demonstrates that arsinothricin is an effective broad-spectrum antibiotic, showing that bacteria have acquired the ability to utilize environmental arsenic to produce a potent antimicrobial. This disclosure shows that arsinothricin is a broad-spectrum antibiotic effective against both Gram-positive and Gram-negative bacteria. Arsinothricin is a non-proteinogenic amino acid analog of glutamate that inhibits bacterial glutamine synthetase. With every new antibiotic, resistance inevitably arises. The arsN1 gene, widely distributed in bacterial arsenic resistance (ars) operons, confers resistance to the herbicide phosphinothricin. The functional linkage of arsN1 to arsenic detoxification was unclear. The disclosure shows that arsN1 selectively confers resistance to arsinothricin. Crystal structures of the ArsN1 N-acetyltransferase elucidate the mechanism of selectivity. These results provide methods of treating infection with arsinothricin or salts of arsinothricin, alone or in combination with an inhibitor of phosphinothricin N-acetyltransferase and arsinothricin N-acetyltransferase.

The instant disclosure demonstrates that an arsenic-containing arsinothricin (2-amino-4-(hydroxymethylarsinoyl) butanoate, AST) (FIG. 1A), produced by the rice rhizosphere microbe *Burkholderia gladioli* GSRB05, has a broad-spectrum antibiotic activity. L-AST and L-PT are non-proteinogenic amino acid analogs of L-glutamate (FIG. 1C). AST is chemically unrelated to other organoarsenicals and can be modified to produce a new class of organoarsenical antibiotics.

Accordingly, certain embodiments of the subject invention provide methods of treating an infection in a subject caused by an infectious agent other than *E. coli*, the method comprising administering to the subject arsinothricin or a salt thereof. Arsinothricin or a salt thereof can be administered in the form of a pharmaceutical composition comprising pharmaceutically acceptable carriers.

Arsinothricin or salts thereof can be administered via, for example, oral, pulmonary, buccal, suppository, intravenous, intraperitoneal, intranasal, intramuscular or subcutaneous routes. Additional routes of administration are well known to a skilled artisan and such embodiments are within the purview of this invention. The appropriate route of administration depends on the type of infection being treated, the subject being treated, the stage and severity of the infection, etc. A person of ordinary skill in the art can determine an appropriate route of administration based on specific parameters.

The infection can be caused by a bacterium, protozoan, helminth, archaebacterial, or a fungus. Preferably, the infectious agent expresses glutamine synthetase.

A bacterium can be Gram-positive or Gran-negative. Non-limiting examples of bacterial infections that can be treated according to the methods of the invention include infections caused by *Burkolderia* spp., *Sinorhizobium* spp., *Schewanella* spp., *Bacillus* spp., *Corynebacterium* spp., *Mycobacterium* spp., and *Enterobacter* spp. Specific bacterial species include *Burkolderia gladioli*, *Sinorhizobium meliloti*, *Schewanella putrefaciens*, *Bacillus cereus*, *Bacillus megaterium*, *Corynebacterium glutamicum*, *Mycobacterium bovis*, *Mycobacterium tuberculosis*, or *Enterobacter cloacae*.

In preferred embodiments the invention provides methods of treating an infection caused by *Mycobacterium tuberculosis* or *Mycobacterium bovis*. In other preferred embodiments, the invention provides methods of treating an infection caused by carbapenem-resistant *Acinetobacter baumannii*, carbapenem-resistant *Pseudomonas aeruginosa*, carbapenem-resistant Enterobacteriaceae (including *Enterobacter cloacae*), vancomycin-resistant *Enterococcus faecium*, methicillin- and/or vancomycin-resistant *Staphylococcus aureus*, clarithrornycin-resistant *Helicobacter pylori*, fluoroquinolone-resistant *Campylobacter* spp., fluoroquinolone-resistant Salmonellae, cephalosporin and/or fluoroquinolone-resistant *Neisseria gonorrhoeae*, penicillin-non-susceptible *Streptococcus pneumoniae*, ampicillin-resistant *Haemophilus influenzae*, fluoroquinolone-resistant *Shigella* spp. or carbapenem-resistant *Enterobacter cloacae*.

In certain embodiments, an infection being treated according the methods disclosed herein is caused by an infectious agent that does not express phosphinothricin N-acetyltransferase or arsinothricin N-acetyltransferase.

In other embodiments, an infection being treated is caused by an infectious agent that expresses phosphinothricin N-acetyltransferase or arsinothricin N-acetyltransferase. In such embodiments, the methods of the invention comprise administering to a subject arsinothricin or a salt thereof in combination with an inhibitor of phosphinothricin N-acetyltransferase or arsinothricin N-acetyltransferase.

In further embodiments, an infectious agent is isolated from a subject and is tested for the expression of phosphinothricin N-acetyltransferase or arsinothricin N-acetyltransferase. If the infectious agent expresses phosphinothricin N-acetyltransferase or arsinothricin N-acetyltransferase, the infection is treated by administering to a subject arsinothricin or a salt thereof in combination with an inhibitor of phosphinothricin N-acetyltransferase or arsinothricin N-acetyltransferase.

Specific examples of inhibitors of phosphinothricin N-acetyltransferase or arsinothricin N-acetyltransferase include 2-({8-fluoro-5H-pyridazino[4,5-b]indol-4-yl}sulfanyl)-N-(1,2,3,4-tetrahydronaphthalen-1-yl)acetamide; 3-oxo-N-({1-phenyl-1H,4H,5H,6H-cyclopenta[c]pyrazol-3-yl}methyl)-3,4-dihydro-2H-1,4-benzothiazine-6-carboxamide; 1-(4-fluorobenzoyl)-N-(3-phenyl-1H-pyrazol-4-yl)piperidine-3-carboxamide; N-[3-({[(6-fluoro-3,4-dihydro-2H-1-benzopyran-4-yl)carbamoyl]amino}methyl)phenyl]cyclobutanecarboxamide; and 1-[1-(2-fluorobenzoyl)piperidin-4-yl]-3-[2-(3-fluorophenyl)cyclopropyl]urea.

Further embodiments of the invention provide a method of killing or inhibiting the growth of an infectious agent other than *E. coli*, the method comprising contacting the infectious agent with an effective amount of arsinothricin or a salt thereof. Specific infectious agents discussed in connection with the methods of treating infections in a subject can be killed or inhibited according to the methods disclosed herein.

Additional embodiments of the invention provide a composition comprising arsinothricin or a salt thereof and an inhibitor of phosphinothricin N-acetyltransferase or arsinothricin N-acetyltransferase. Specific inhibitors of phosphinothricin N-acetyltransferase or arsinothricin N-acetyltransferase identified above can be used in the compositions of the invention. In certain embodiments, the compositions comprising arsinothricin or a salt thereof and an inhibitor of phosphinothricin N-acetyltransferase or arsinothricin N-acetyltransferase further comprise pharmaceutically acceptable carriers or excipients.

Routes of Administration and Dosage Forms

In certain embodiments, arsinothricin or a salt thereof, optionally, in combination with an inhibitor of phosphinothricin N-acetyltransferase or arsinothricin N-acetyltransferase, may be administered intramuscularly, subcutaneously, intrathecally, intravenously or intraperitoneally by infusion or injection. Solutions of arsinothricin or a salt thereof can be prepared in water, optionally mixed with a nontoxic surfactant. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising arsinothricin or a salt thereof, optionally, in combination with an inhibitor of phosphinothricin N-acetyltransferase or arsinothricin N-acetyltransferase, that are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating arsinothricin or a salt thereof, optionally, in combination with an inhibitor of phosphinothricin N-acetyltransferase or arsinothricin N-acetyltransferase, in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder of arsinothricin or a salt thereof, optionally, in combination with an inhibitor of phosphinothricin N-acetyltransferase or arsinothricin N-acetyltransferase, plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the subject's diet.

For oral therapeutic administration, arsinothricin or a salt thereof, optionally, in combination with an inhibitor of phosphinothricin N-acetyltransferase or arsinothricin N-acetyltransferase, may be combined with one or more excipients and used in the form of ingestible tablets, buccal tablets, troches, capsules, elixirs, suspensions, syrups, wafers, and the like. Such compositions and preparations should contain at least 0.1% of arsinothricin or a salt thereof of the present invention. The percentage of arsinothricin or a salt thereof present in such compositions and preparations may, of course, be varied and may conveniently be between about 2% to about 60% of the weight of a given unit dosage form. The amount of arsinothricin or a salt thereof in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir may contain arsinothricin or a salt thereof, optionally, in combination with an inhibitor of phosphinothricin N-acetyltransferase or arsinothricin N-acetyltransferase, and sucrose or fructose as a sweetening agent, methyl and propylparabens as preservatives, a dye, and flavoring such as cherry or orange flavor.

Of course, any material used in preparing any unit dosage form should be pharmaceutically acceptable and substantially non-toxic in the amounts employed.

In addition, arsinothricin or a salt thereof, optionally, in combination with an inhibitor of phosphinothricin N-acetyltransferase or arsinothricin N-acetyltransferase, may be incorporated into sustained-release preparations and devices. For example, arsinothricin or a salt thereof, optionally, in combination with an inhibitor of phosphinothricin N-acetyltransferase or arsinothricin N-acetyltransferase, may be incorporated into time release capsules, time release tablets, time release pills, and time release polymers or nanoparticles.

Pharmaceutical compositions for topical administration of arsinothricin or a salt thereof, optionally, in combination with an inhibitor of phosphinothricin N-acetyltransferase or arsinothricin N-acetyltransferase, to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which arsinothricin or a salt thereof, optionally, in combination with an inhibitor of phosphinothricin N-acetyltransferase or arsinothricin N-acetyltransferase, can be dissolved or dispersed at effective levels, optionally with the aid of non-toxic surfactants.

Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions that can be used to deliver arsinothricin or a salt thereof, optionally, in combination with an inhibitor of phosphinothricin N-acetyltransferase or arsinothricin N-acetyltransferase, to the skin are known in the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of arsinothricin or a salt thereof, optionally, in combination with an inhibitor of phosphinothricin N-acetyltransferase or arsinothricin N-acetyltransferase, in such formulations can vary widely depending on the nature of the formulation and intended route of administration. For example, the concentration of arsinothricin or a salt thereof, optionally, in combination with an inhibitor of phosphinothricin N-acetyltransferase or arsinothricin N-acetyltransferase, in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises arsinothricin or a salt thereof, optionally, in combination with an inhibitor of phosphinothricin N-acetyltransferase or arsinothricin N-acetyltransferase, and further in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing arsinothricin or a salt thereof, optionally, in combination with an inhibitor of phosphinothricin N-acetyltransferase or arsinothricin N-acetyltransferase, in further combination with carriers known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise arsinothricin or a salt thereof, optionally, in combination with an inhibitor of phosphinothricin N-acetyltransferase or arsinothricin N-acetyltransferase, in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising arsinothricin or a salt thereof, optionally, in combination with an inhibitor of phosphinothricin N-acetyltransferase or arsinothricin N-acetyltransferase. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of arsinothricin or a salt thereof, optionally, in combination with an inhibitor of phosphinothricin N-acetyltransferase or arsinothricin N-acetyltransferase.

Arsinothricin or a salt thereof, optionally, in combination with an inhibitor of phosphinothricin N-acetyltransferase or arsinothricin N-acetyltransferase, may be combined with an inert powdered carrier and inhaled by the subject or insufflated.

Pharmaceutical compositions for administration by inhalation or insufflation can be provided in the form of a dry powder composition, for example, a powder mix of arsinothricin or a salt thereof, optionally, in combination with an inhibitor of phosphinothricin N-acetyltransferase or arsinothricin N-acetyltransferase, and a suitable powder base such as lactose or starch. Such powder composition can be provided in unit dosage form, for example, in capsules, cartridges, gelatin packs, or blister packs, from which the powder can be administered with the aid of an inhalator or insufflator.

The exact amount (effective dose) of arsinothricin or a salt thereof, optionally, in combination with an inhibitor of phosphinothricin N-acetyltransferase or arsinothricin N-acetyltransferase, can vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

Arsinothricin or a salt thereof, optionally, in combination with an inhibitor of phosphinothricin N-acetyltransferase or arsinothricin N-acetyltransferase, can be conveniently administered in unit dosage form, containing for example, about 0.05 to about 10000 mg, about 0.5 to about 10000 mg, about 5 to about 1000 mg, or about 50 to about 500 mg of each of arsinothricin or a salt thereof or the inhibitor of phosphinothricin N-acetyltransferase or arsinothricin N-acetyltransferase per unit dosage form.

Arsinothricin or a salt thereof, optionally, in combination with an inhibitor of phosphinothricin N-acetyltransferase or arsinothricin N-acetyltransferase, can be administered to achieve peak plasma concentrations of, for example, from about 0.25 to about 200 µM, about 0.5 to about 75 µM, about 1 to about 50 µM, about 2 to about 30 µM, or about 5 to about 25 µM of each of arsinothricin or a salt thereof or the inhibitor of phosphinothricin N-acetyltransferase or arsinothricin N-acetyltransferase per unit dosage form. Exemplary desirable plasma concentrations include at least 0.25, 0.5, 1, 5, 10, 25, 50, 75, 100 or 200 µM. For example, plasma levels may be from about 1 to about 100 micromolar or from about 10 to about 25 micromolar. This may be achieved, for example, by the intravenous injection of a 0.05 to 5% solution of arsinothricin or a salt thereof, optionally, in combination with an inhibitor of phosphinothricin N-acetyltransferase or arsinothricin N-acetyltransferase, optionally in saline, or orally administered as a bolus containing about 1 to about 100 mg of arsinothricin or a salt thereof, optionally, in combination with an inhibitor of phosphinothricin N-acetyltransferase or arsinothricin N-acetyltransferase. Desirable blood levels may be maintained by continuous or intermittent infusion.

Arsinothricin or a salt thereof, optionally, in combination with an inhibitor of phosphinothricin N-acetyltransferase or arsinothricin N-acetyltransferase, can be included in the compositions within a therapeutically useful and effective concentration range, as determined by routine methods that are well known in the medical and pharmaceutical arts. For example, a typical composition can include arsinothricin or a salt thereof, optionally, in combination with an inhibitor of phosphinothricin N-acetyltransferase or arsinothricin N-acetyltransferase, at a concentration in the range of at least about 1 mg/ml, preferably at least about 4 mg/ml, more preferably at least 5 mg/ml and most preferably at least 6 mg/ml of each of arsinothricin or a salt thereof or the inhibitor of phosphinothricin N-acetyltransferase or arsinothricin N-acetyltransferase.

Arsinothricin or a salt thereof, optionally, in combination with an inhibitor of phosphinothricin N-acetyltransferase or arsinothricin N-acetyltransferase, may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with arsinothricin or a salt thereof, optionally, in combination with an inhibitor of phosphinothricin N-acetyltransferase or arsinothricin N-acetyltransferase.

Definitions

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., subranges within the disclosed range), specific embodiments therein are intended to be explicitly included.

"Treatment" or "treating" (and grammatical variants of these terms), as used herein, refer to an approach for obtaining beneficial or desired results including but not limited to therapeutic benefit. A therapeutic benefit is achieved with the eradication or amelioration of one or more of the physiological symptoms associated with the underlying infection such that an improvement is observed in the subject, notwithstanding that the subject may still be afflicted with the underlying infection.

The term "effective amount" or "therapeutically effective amount" refers to that amount of arsinothricin or a salt thereof, optionally, in combination with an inhibitor of phosphinothricin N-acetyltransferase or arsinothricin N-acetyltransferase, described herein that is sufficient to effect treatment of the infection. The therapeutically effective amount may vary depending upon the intended application, the subject, and the infection being treated, e.g., the weight and age of the subject, the severity of the infection, the manner of administration and the like, which can readily be determined by one of ordinary skill in the art. The specific dose will vary depending on the particular dosing regimen to be followed, whether it is administered in combination with other compounds, timing of administration, the tissue to which it is administered, and the physical delivery system in which it is carried.

A "sub-therapeutic amount" of arsinothricin or a salt thereof, optionally, in combination with an inhibitor of phosphinothricin N-acetyltransferase or arsinothricin N-acetyltransferase, is an amount less than the effective amount for arsinothricin or a salt thereof, optionally, in combination with an inhibitor of phosphinothricin N-acetyltransferase or arsinothricin N-acetyltransferase, but which when combined with an effective or sub-therapeutic amount of another agent or therapy can produce a desired result, due to, for example, synergy in the resulting efficacious effects (e.g., therapeutic benefit) for the subject, or reduced side effects associated with the compounds administered to the subject. Typical therapeutic amounts for arsinothricin or a salt thereof, optionally, in combination with an inhibitor of phosphinothricin N-acetyltransferase or arsinothricin N-acetyltransferase, can be ascertained from various publicly available sources and/or routine experimentation.

A "synergistically effective" therapeutic amount or "synergistically effective" amount of arsinothricin or a salt thereof, optionally, in combination with an inhibitor of phosphinothricin N-acetyltransferase or arsinothricin N-acetyltransferase, is an amount which, when combined with an effective or subtherapeutic amount of another agent or therapy, produces a greater effect than when either of the two agents are used alone. A synergistically effective therapeutic amount of arsinothricin or a salt thereof, optionally, in combination with an inhibitor of phosphinothricin N-acetyltransferase or arsinothricin N-acetyltransferase, produces a greater effect when used in combination than the additive effects of each of the two agents or therapies when used alone. The term "greater effect" encompasses not only a reduction in symptoms of the infection to be treated, but also reduced side effects, improved tolerability, improved subject compliance, improved efficacy, or any other improved clinical outcome.

As used herein, "therapeutic agent" refers to arsinothricin or a salt thereof, optionally, in combination with an inhibitor of phosphinothricin N-acetyltransferase or arsinothricin N-acetyltransferase. The salts can be with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in arsinothricin or salts of arsinothricin is either replaced by a metal ion, e.g., an alkali metal ion, an alkaline earth ion, a selenium ion or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like.

The terms "co-administration," "administered in combination with," and their grammatical equivalents encompass administration of two or more agents to a subject so that both agents and/or their metabolites are present in the subject at the same time. Co-administration includes simultaneous administration in separate compositions, administration at different times in separate compositions, or administration in a composition in which both agents are present. Co-administered agents may be in the same formulation. Co-administered agents may also be in different formulations.

A "therapeutic effect," as used herein, encompasses a therapeutic benefit as described above. This includes delaying the appearance of an infection, delaying the onset of symptoms of an infection, slowing, halting, or reversing the progression of an infection, or any combination thereof.

"Pharmaceutically acceptable carrier" or "pharmaceutically acceptable excipient" includes any and all solvents, dispersion media, coatings, antibacterial and antifungal agents, isotonic, and absorption delaying agents, and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Subject" refers to an animal, such as a mammal, for example a human. The methods described herein can be useful in both pre-clinical human therapeutics and veterinary applications. In some embodiments, the subject is a mammal (such as an animal model of disease), and in some embodiments, the subject is human. Non-limiting examples of subjects include canine, porcine, rodent, feline, bovine, poultry, equine, human, and a non-human primate.

The terms "simultaneous" or "simultaneously" as applied to administering agents to a subject refer to administering one or more agents at the same time, or at two different time points that are separated by no more than 1 hour. The term "sequentially" refers to administering more than one agent at two different time points that are separated by more than 1 hour, e.g., about 2 hours, about 5 hours, 8 hours, 1 day, 2 days, 3 days, 4 days, 5 days, 6 days, 7 days or even longer.

Materials and Methods

Reagents

All reagents and enzymes were purchased from Sigma-Aldrich Co. LLC (St. Louis, Mo., USA), unless otherwise stated. Arsinothricin (AST) was purified from culture of *B. gladioli* GSRB05 as described previously. The concentration of purified AST was determined by inductively coupled plasma mass spectrometry (ELAN DRC-e; Perkin-Elmer, Waltham, Mass., USA). Arsinothricin was assumed to be the L-enantiomer based on the protein-bound crystal structure (vide infra). Phosphinothricin (PT) and methionine S-sulfoximine (MSO) used were D,L-enantiomer (glufosinate ammonium, considered as 1:1 mixture of D- and L-enantiomers) and L-enantiomers, respectively. The PT concentration is indicated as L-PT because only the L-enantiomer is functional. Methylarsonous acid (MAs(III)) was prepared as described previously.

Bacterial Strains

Escherichia coli strains DH5a (Promega, Madison, Wis., USA) and TOP10 (Invitrogen, Waltham, Mass., USA) were used for gene cloning and protein expression, respectively. E. coli strain W3110 and the ars operon deleted derivative AW3110 (Δars), Pseudomonas putida KT2440 and the double ars operon deleted derivative strain (Δars1,2), Burkholderia gladioli GSRB05, Shinorhizobium meliloti Rm1021, Shewanella putrefaciens 200, Bacillus cereus UW85, Bacillus megaterium (ATCC 14581), Corynebacterium glutamicum (ATCC 13032), Enterobacter cloacae (ATCC BAA-2341) and Mycobacterium bovis BCG (ATCC 19274) were used for in vivo resistance assays.

Cloning, Expression and Protein Purification

For gene cloning and protein expression, E. coli cells were grown at 37° C. in lysogeny broth (LB) medium supplemented with 0.1 mg/ml ampicillin. For construction of a plasmid for expression of arsN1 from Pseudomonas putida KT2440 (PparsN1) (Accession number AAN67541.1) in fusion with a six histidine tag at C-terminus, a 558-bp fragment excluding the stop codon was PCR-amplified from total genomic DNA of P. putida KT2440 by high fidelity Pfu Turbo DNA polymerase (Agilent Technologies Inc., Santa Clara, Calif., USA) using the forward primer 5'-CCAG<u>CCATGG</u>ATAGCGGAATCGATATTCG-3' (SEQ ID NO: 1, NcoI site underlined) and reverse primer 5'-CCAG<u>AAGCTT</u>ACGAGGCACTGGGATTTGG-3' (SEQ ID NO: 2, HindIII site underlined) and then ligated into pBAD-Myc/Iis-A as an NcoI/HindIII digest, generating the plasmid pBAD-PparsN1. The DNA sequence for pat the gene encoding phosphinothricin N-acetyltransferase from Storeptomyces viridochromeogenes (Svpat) (Accession number AAU00088.1) with six histidine codons inserted at the 3' end before the stop codon was chemically synthesized by GenScript (NJ, USA) with 5' NcoI and 3' HindIII sites and subcloned into the EcoRV site of pUC57-Kan (pUC57-Kan-Svpat). The synthetic Svpat gene was cloned as an NcoI/HindIII digest from pUC57-Kan-Svpat into pBAD-Myc/His-A, generating plasmid pBAD-Svpat. Cells of E. coli TOP10 bearing pBAD-PparsN1 or pBAD-Svpat were grown in LB medium with shaking at 37° C. At an $A_{600\,nm}$ of 0.5-0.6, L-arabinose was added as an inducer at a final concentration of 0.2%. After 5 h, the cells were harvested and stored at −80° C. until use. The frozen cells were thawed and washed once with and suspended in buffer A (50 mM morpholinopropane-1-sulfonic acid (MOPS), pH 7.5, containing 20 mM imidazole, 0.5 M NaCl and 20% (v/v) glycerol) (5 ml per g of wet cells). The cells were lysed by a single passage through a French pressure cell at 20,000 psi and immediately treated with diisopropylfluorophosphate (2.5 μl per g of wet cell). The cell lysate was centrifuged at 40,000 rpm using a T865 rotor (Thermo Fisher Scientific, Waltham, Mass., USA) for 60 min at 4° C. The supernatant solution was applied onto a Ni-NTA column (QIAGEN Sciences, Hilden, Germany) at a flow rate of 1.0 ml/min and washed with 20 column volumes (100 ml) of buffer A. Bound protein was eluted with buffer A containing 0.2 M imidazole, and the purity was analyzed by sodium dodecyl sulfate polyacrylamide gel electrophoresis. Protein concentrations were estimated by the method of Bradford using bovine serum albumin as a standard. Fractions containing the protein were pooled and concentrated using a 10 kDa Amicon Ultra centrifugal filter (EMD Millipore, Billerica, Mass., USA). The concentrated protein was rapidly frozen and stored at −80° C. until use.

Glutamine Synthetase Assays

The activity of glutamine synthetase (GS) from E. coli was measured using a coupled assay which determines the formation of the product adenosine 5'-diphosphate (ADP) to oxidize reduced form of β-nicotinamide adenine dinucleotide (NADH). 1 ml reaction mixture contained 34.1 mM imidazole, 8.5 mM ATP, 1.1 mM phosphoenolpyruvate, 60 mM magnesium chloride, 18.9 mM potassium chloride, 45 mM ammonium chloride, 0.25 mM NADH, 12.6 to 19.6 units of L-lactic dehydrogenase, and 8.4 to 14 units of pyruvate kinase. The reaction was initiated by addition of GS at 0.2 nM, final concentration. The decrease in $A_{340\,nm}$ was measured at 37° C., and the oxidation of NADH to $NAD^+$ was quantified using the extinction coefficient 6230 $M^{-1}\,cm^{-1}$. The assays were done with varying concentrations of L-glutamate from 2 to 100 mM. The inhibitor constants ($K_i$) for AST and PT were determined by measuring the apparent $K_m$ of GS with three different concentrations of inhibitor. Activities were corrected with the values from no enzyme controls. Kinetic constants were calculated using Sigma Plot. Data are the mean±SE (n=3).

N-acetyltransferase Assays

The enzymatic activity of purified PpArsN1 was measured from the rate of 5,5'-dithio-bis-2-nitrobenzoic acid (DTNB) reduction, as described previously with minor modifications.

The reactions were carried out in 20 mM Tris-HCl (pH 7.4), 1 mM EDTA, 0.33 mM DTNB, 0.2 mM acetyl-CoA (AcCoA) with 50 μM AST, PT or MSO at 37° C. The reactions were initiated by addition of AcCoA and the increase in $A_{412\,nm}$ was measured over the first 2 min. The specific activity was determined using the molar extinction coefficient of 2-nitro-5-benzoatic acid (14,150 $M^{-1}\,cm^{-1}$). Activities were corrected with the values from no enzyme controls. The kinetics of PpArsN1 and SvPAT for PT and AST were determined over a concentration range between 1 μM and 2 mM using 0.2 μM enzyme. Kinetic constants were calculated from a fit of the data to the Michaelis-Menten equation. Data are the mean±SE (n=3).

Bacterial Resistance Assays

Middlebrook 7H9 broth (Difco Laboratories Inc., Detroit, Mich., USA) supplemented with 5 g BSA, 2 g dextrose, 0.85 g NaCl, and 0.05% tween 80 (Fisher Scientific International Inc., Pittsburgh, Pa., USA) was used for M. bovis BCG culture. Mycobacterial cells were inoculated at a density of $1.0\times10^5$ CFU/ml and horizontally cultured in the presence or absence of indicated concentrations of AST, PT or MSO in an incubator humidified at 37° C. under 5% $CO_2$ for up to 4 weeks. Viable cells in each culture were weekly determined by $A_{600\,nm}$. All the other bacterial strains were grown in LB medium to log phase ($A_{600\,nm}$ 0.6-0.8), following which the cells were centrifuged, and then washed with and suspended in M9 medium to an $A_{600\,nm}$ of 0.04-0.06 with or without the indicated concentrations of As(III), MAs(III), AST, PT, or MSO. M9 medium was supplemented with 0.2% citrate (w/v) and 20 μg/ml uracil for P. putida strains, while M9 medium supplied with 0.2% glucose (w/v) was used for the other bacterial strains. 0.1 mg/ml ampicillin and 0.2% arabinose were added to E. coli culture as antibiotics and inducer as required. Resistance was determined from the $A_{600\ nm}$ after 24 h. *E. coli* and *B. megaterium* were grown at 37° C., whereas the other examined bacterial strains were all cultured at 30° C.

Cytotoxicity Assays

Human acute monocytic leukemia THP-1 cells (ATCC TIB-202™) were seeded in a 24-well plate (Nalge Nunc International, Rochester, N.Y., USA) with 300 µl of RPMI-1640 medium (Lonza, Basel, Switzerland) supplemented with 10% fetal bovine serum and 0.05 mM 2-mercaptoethaol at a density of $1.0\times10^5$ cells/well and cultured in a 5% $CO_2$ humidified incubator at 37° C. After 24 h, THP-1 cells were further cultured in the presence or absence of the indicated concentrations of AST or As(III) for another 24 h, following which viability of cells was investigated by a 3-(4,5-dimethylthiazol-2-yl) 2,5-diphenyltetrazolium bromide (MTT) assay. MTT was added to each well at a final concentration of 0.5 mM and incubated for 3 h. The plate was then centrifuged at 400×g and the cell pellets were completely lysed with 300 µl of dimethyl sulfoxide. $A_{570\ nm}$ of each condition was measured and compared. Data are the mean±SE (n=4).

ArsN1 Distribution and Phylogenetic Analysis

The prevalence of arsN1 genes in ars operon were analyzed in the representative organisms. GenBank accession numbers of bacterial genomes are given in parentheses. *Pseudomonas putida* KT2440 (AE015451), *Acidovorax* sp. CF316 (AKJX00000000), *Porphyrobacter mercurialis* (JTDN00000000), *Pseudomonas syringae* pv. *syringae* B728a (CP000075), *Inquilinus limosus* DSM 16000 (AUHM00000000), *Sphingopyxis* sp. KK2 (LYVN00000000), *Sphingomonas yabuuchiae* (LDTF00000000), *Pelomonas* sp. KK5 (LYVQ00000000). For phylogenetic analysis, multiple alignment of the sequences of N-acetyltransferase homologs was performed using Clustal Omega (see world-wide website: ebi.ac.uk/Tools/msa/clustalo/). ArsN1 sequences distributed in ars operons were selected for phylogenetic analysis. Acquisition of sequences was performed by searching a list of reference organisms or from the National Center for Biotechnology (NCBI) protein database by BLASTP search. Phylogenetic analysis was performed to infer the evolutionary relationship among the ArsN1 sequences of various organisms. The phylogenetic tree was constructed using the Neighbor-Joining method using MEGA 6.0.1. The statistical significance of the branch pattern was estimated by conducting a 1000 bootstrap. GenBank accession numbers of ArsN1 orthologs are given in parentheses. *Pseudomonas putida* KT2440 (WP_010952945, WP_010955452), *Acidovorax* sp. CF316 (WP_007857208), *Porphyrobacter mercurialis* (WP_039093634), *Pseudomonas syringae* pv. *syringae* B728a (YP_234588), *Inquilinus limosus* DSM 16000 (WP_026871525), *Sphingopyxis* sp. KK2 (WP_077145629), *Sphingomonas yabuuchiae* (WP_058746517), *Pelomonas* sp. KK5 (WP_077035561), *Streptomyces hygroscopicus* (P16426), *Streptomyces viridochromogenes* (WP_003988626), *Streptomyces coelicolor* A3(2) (CAB90987), *Pseudomonas aeruginosa* PAO 1 (AAG08251), *Salmonella enterica* (WP_061381307).

Crystallization, Data Collection, Structure Solution, and Refinement

Initial crystal screening was performed by the sitting-drop vapor-diffusion method using a variety of crystal screens from Hampton Research (Aliso Viejo, Calif., USA), Emerald BioSystems, Inc. (Bainbridge Island, Wash., USA) and Jena Bioscience GmbH (Jena, Germany) in 96-well plates (Corning Inc., Corning, N.Y., USA) at 293 K. Crystalline precipitates were obtained at 0.2 M sodium acetate, 0.1M Tris-HCl, pH 8.5, and 30% PEG 4000. Diffraction quality crystals were grown using the vapor diffusion hanging drop method in 24-well Linbro plates. The reservoir solution (0.3 ml) consisted of 0.2 M sodium acetate, 0.1 M Tris-HCl and 20% PEG 6000, and the hanging drop contained 2 µl of 20 mg/ml of purified PpArsN1, 2 µl reservoir solution and 1 µl of 0.1 M ATP. Rod-shaped crystals with approximate dimensions of 0.1×0.05×0.05 mm were obtained within a few weeks. The PpArsN1-AST complex was prepared by adding 0.5 ml of 4.0 mM AST to 0.5 ml of 1 mM protein. PpArsN1-AST crystals were grown using a vapor diffusion hanging drop method. The hanging drop contained 2 µl of PpArsN1-AST complex and 2 µl of reservoir solution. The reservoir contained 1.5 M sodium formate and 0.1 M sodium acetate with pH 4.5. Thin plates like crystals were obtained within a week. The PpArsN1-PT complex was prepared by adding 0.5 ml of 50.0 mM PT to 0.5 ml of 1 mM protein. The PpArsN1-PT crystals were also grown using the same method and same crystallization condition used for PpArsN1-AST. The crystals were harvested from the hanging drop using a cryoLoop, flash-frozen in liquid nitrogen at 100 K and stored in liquid nitrogen. Ethylene glycol (20%) was used as cryoprotectant. X-ray data were collected on beamline 22ID at the Advanced Photon Source (APS), Argonne National laboratory, using a MAR300HS detector. The crystal-to-detector distance was 180 mm, and 180 images for PpArsN1 crystal, 240 and 360 images for PpArsN1-AST and PpArsN1-PT crystals, respectively, were collected with 10 oscillation. The PpArsN1 diffraction data were indexed and scaled using KYLIN and PpArsN1-AST and PpArsN1-PT data were indexed and scaled using HKL2000. The data processing statistics are shown in Table 1. The PpArsN1 crystal diffracted to 2.16 Å resolution. The crystal belongs to space group $P4_32_12$ with cell dimensions a=b=67.02 Å, c=206.74 Å. The Matthews coefficient of 2.48 indicates that there are two molecules in the asymmetric unit with 50.5% solvent. An initial homology model was constructed by molecular replacement using SWISS-MODEL (PDB ID: 1YVO as a template with 32.3% identity). Molecular replacement was done using PHASER in the CCP4 suite. The initial R and $R_{free}$ are 35.0 and 40.0%, respectively. The structure was refined using PHENIX. The C-terminal extended residues were fitted in electron density using COOT. Water molecules were added at appropriate positions and refined. The final R and $R_{free}$ are 23.7 and 26.6%, respectively. The PpArsN1-AST crystal diffracted up to 2.19 Å resolution and indexed with C121 space group with cell dimensions a=185.27, b=141.74, c=54.55 Å, and β=90.6°. The Matthews coefficient of 2.54 indicates that there are six molecules in the asymmetric unit with 51.6% solvent. The PpArsN1-Apo structure was used as model for molecular replacement. There are positive electron densities at the 9.0 and 16.0 σ level near Arg77 in molecule A and B, respectively (FIG. 6). The density was fitted with AST, and the anomalous difference map confirmed the presence of arsenic. The PpArsN1-PT crystal diffracted up to 2.66 Å resolution and indexed with $P12_11$ space group with cell dimensions a=53.84, b=142.69, c=178.31 Å, and (β=89.9°. The Matthews coefficient of 2.45 indicates that there are twelve molecules in the asymmetric unit with 49.8% solvent. The PpArsN1-Apo structure was used as model for molecular replacement. There are positive electron densities between 6.5 to 9.0 σ level near Arg77 in molecule A, B, C, D, G, H, I, and J (FIG. 7). The density was fitted with PT molecules. The structures were refined using REFMAC 5 in the CCP4 suite. The simulated annealing refinement was done using PHENIX. The structure factor and coordinates were deposited to protein data bank (PDB ID: 5JTF and 5 WPH). The molecules were drawn with PyMol (Version 1.8 Schrödinger, LLC). Docking was performed using AutoDockTools and AutoDock4.

TABLE 1

X-ray data indexing and refinement statistics. (Values in parenthesis are highest resolution shell.)

| Data collection | PpArsN1 | PpArsN1-AST | PpArsN1-PT |
| --- | --- | --- | --- |
| PDB ID | 5JTF | 5WPH | |
| Source | APS 22ID | APS 22ID | APS 22ID |
| Wavelength (Å) | 1.0000 | 1.0000 | 1.0000 |
| Resolution range (Å) | 30.64-2.16 (2.20-2.16) | 50.00-2.19 (2.23-2.19) | 39.91-2.66 (2.75-2.66) |
| Space group | $P4_32_12$ | C121 | P1211 |
| Unit cell parameters (Å, °) | a = b = 67.02, c = 206.74 | a = 185.27, b = 141.74, c = 54.55, β = 90.6 | a = 53.84, b = 142.69, c = 178.31, β = 89.9 |
| Unique reflections | 25849 | 72209 | 75010 |
| Completeness (%) | 97.6 (90.8) | 99.4 (95.7) | 97.0 (97.2) |
| Redundancy | 5.16 (4.31) | 7.3 (4.4) | 4.2 (3.9) |
| $R_{meas}$ | 0.087 (0.342) | 0.161 (0.739) | 0.178 (1.320) |
| I/σI | 6.9 (2.9) | 12.4 (1.9) | 11.0 (1.9) |
| Refinement | | | |
| $R/R_{free}$ | 0.237/0.266 | 0.180/0.232 | 0.224/0.272 |
| RMSD | | | |
| Bonds (Å) | 0.004 | 0.013 | 0.004 |
| Angles (°) | 0.905 | 1.477 | 0.880 |
| Average B-factor Å$^2$ | 35.0 | 30.0 | 39.5 |
| Ramachandran plot (%) | | | |
| Most favored | 93.0 | 96.0 | 93.8 |
| Allowed | 6.3 | 2.0 | 4.6 |
| Outliers | 1.7 | 1.0 | 1.7 |

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—AST is a Broad-Spectrum Antibiotic

To determine whether AST has antibiotic activity, its ability to inhibit growth of bacteria was examined using environmental isolates. AST was equally effective against both Gram-negative and Gram-positive bacteria, and 15-fold more potent than commercial PT (FIG. 2A).

Figure 2B:
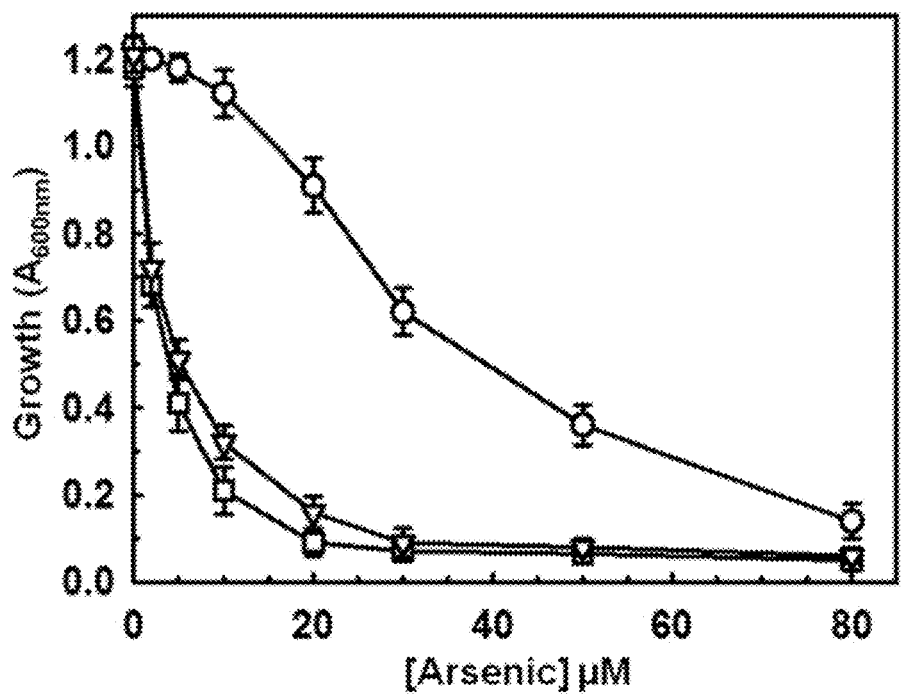

Each species was inhibited to the same degree by 25 μM AST as 400 μM PT except for *B. gladioli* GSRB05 and *P. putida* KT2440. *B. gladioli* GSRB05 is the producer of AST, so it is not unexpected that this strain has a resistance mechanism. As discussed below, the arsN1 gene confers resistance in *P. putida* KT2440. In *E. coli*, AST is considerably more inhibitory than inorganic As(II) and is similar to that of highly toxic trivalent methylarsenite (MAs(III)) (FIG. 2B). Given that in general pentavalent arsenicals are relatively benign and much less toxic compared to trivalent species, this is a striking result particularly because except thiolated species, AST would be the only known pentavalent arsenic species that exhibits such an extremely high toxicity.

Example 2—AST Inhibits Glutamine Synthetase

The mechanism of action of PT is irreversible inhibition of bacterial glutamine synthetase (GS). PT also inhibits plant GS and is sold as the broad-spectrum systemic herbicide Glufosinate. Because of the structural analogy with PT (FIG. 1), the target molecule of AST is hypothesized herein to be bacterial GS. Thus, the effect of AST and PT on purified *E. coli* GS activity was examined. The $K_m$ of GS was found to be 2.7±0.64 mM. The observed $K_i$ values for AST and PT are 0.3±0.05 μM and 0.4±0.15 μM, respectively, indicating that AST is an effective inhibitor of GS.

Example 3—AST is Effective on Pathogenic Bacteria

Figure 2C:
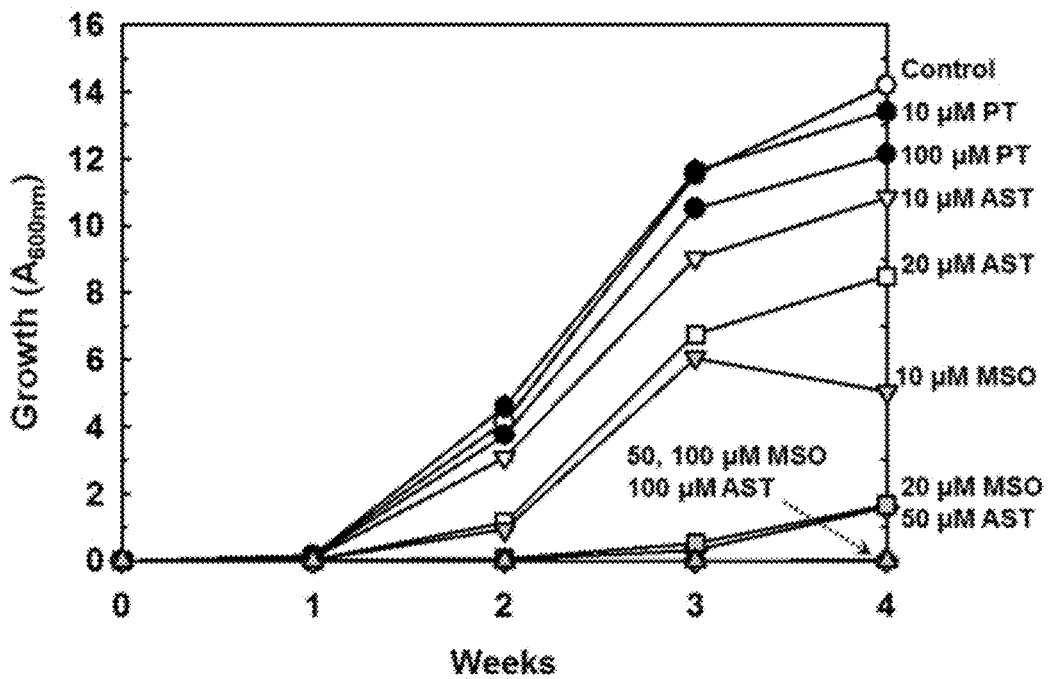
Figure 2D:
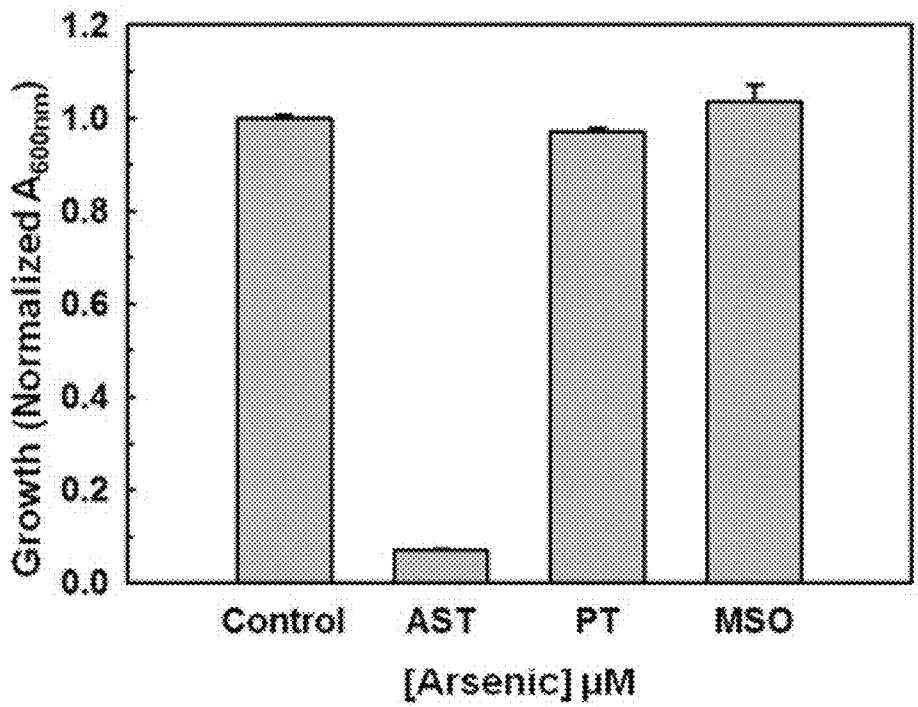
Figure 2E:
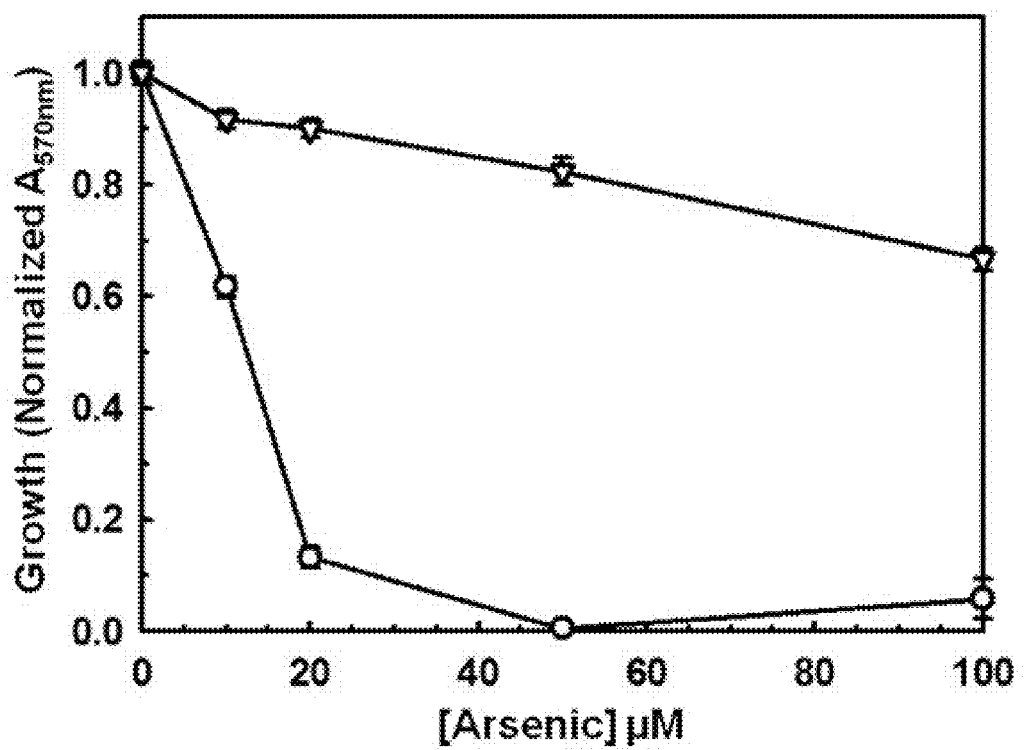

Inhibition of GS has been indicated as a novel therapeutic strategy against TB. Pathogenic mycobacteria including MTB secrete large amounts of extracellular GS that is involved in synthesis of poly-α-L-glutamine (PLG) layer, a cell wall component that is found exclusively in pathogenic strains and considered essential to their virulence. Methionine sulfoximine (MSO, FIG. 1D), the first GS inhibitor described, effectively inhibited MTB growth both in vitro as well as in vivo. To examine the potential of AST as a drug for TB, AST effect on a related pathogenic strain *Mycobacterium bovis* BCG was analyzed and compared with PT and MSO (FIG. 2C). AST exhibited an inhibitory effect on mycobacterial growth, which is comparable with MSO and much higher than PT. AST also effectively inhibited the growth of carbapenem-resistant *Enterobacter cloacae* (ATCC BAA-2341), which belongs to the highest priority category in the WHO global priority pathogens list, whereas other GS inhibitors have no effects (FIG. 2D). Among the tested GS inhibitors, only AST effectively inhibited growth of both *Mycobacterium* and *Enterobacter* pathogens, which strongly indicates that AST can be developed further to produce new potent antimicrobial drugs against drug-resistant pathogens. AST on human monocytes was benign and much less toxic compared to inorganic arsenite (FIG. 2E), which further supports the high potential of AST as a lead compound for drug development because the side effects should be minor.

Example 4—PpArsN1 Confers Resistance to Phosphinothricin and Arsinothricin

Figure 3A:
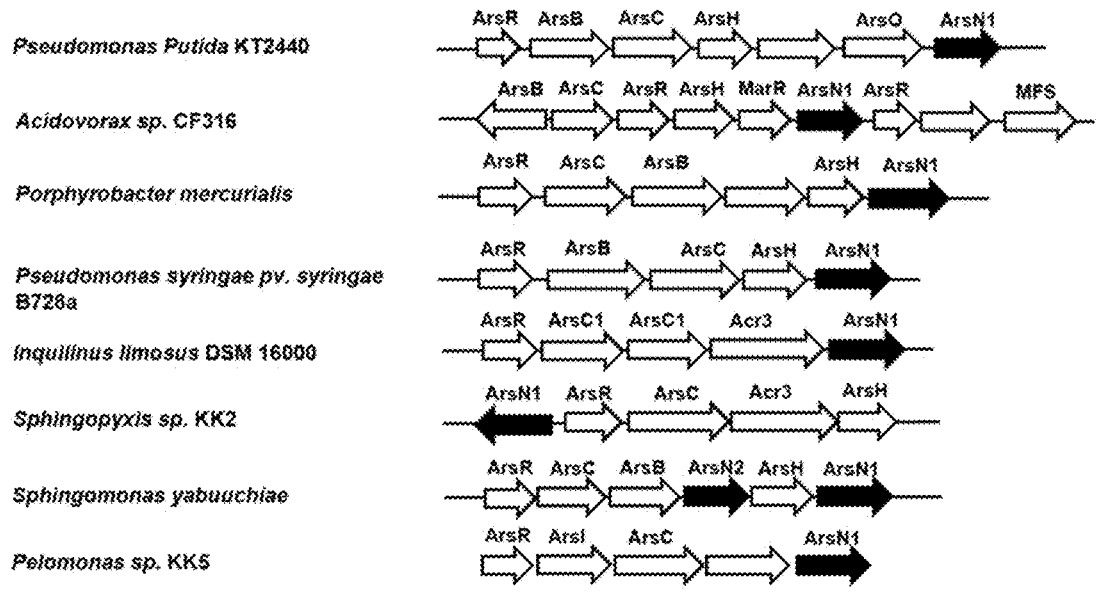
Figure 3B:
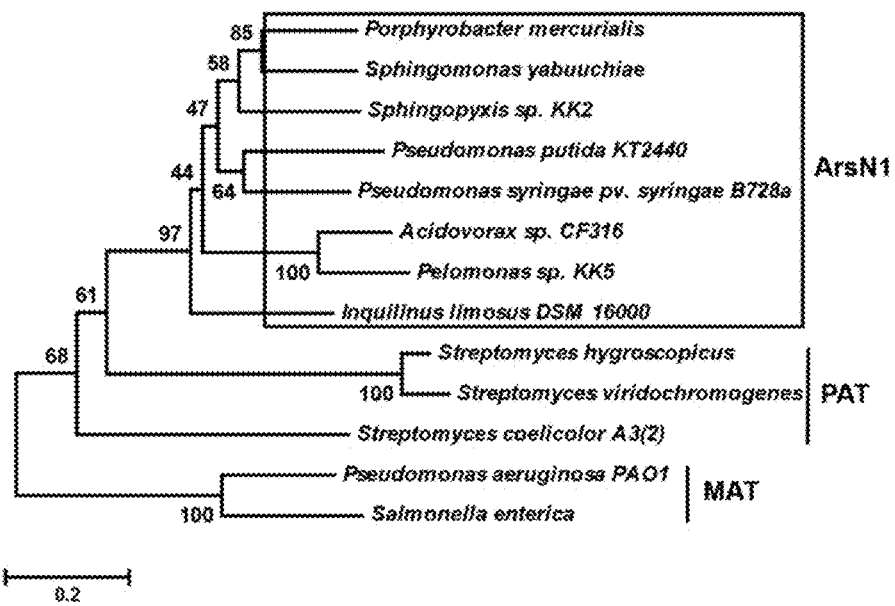
Figure 3C:
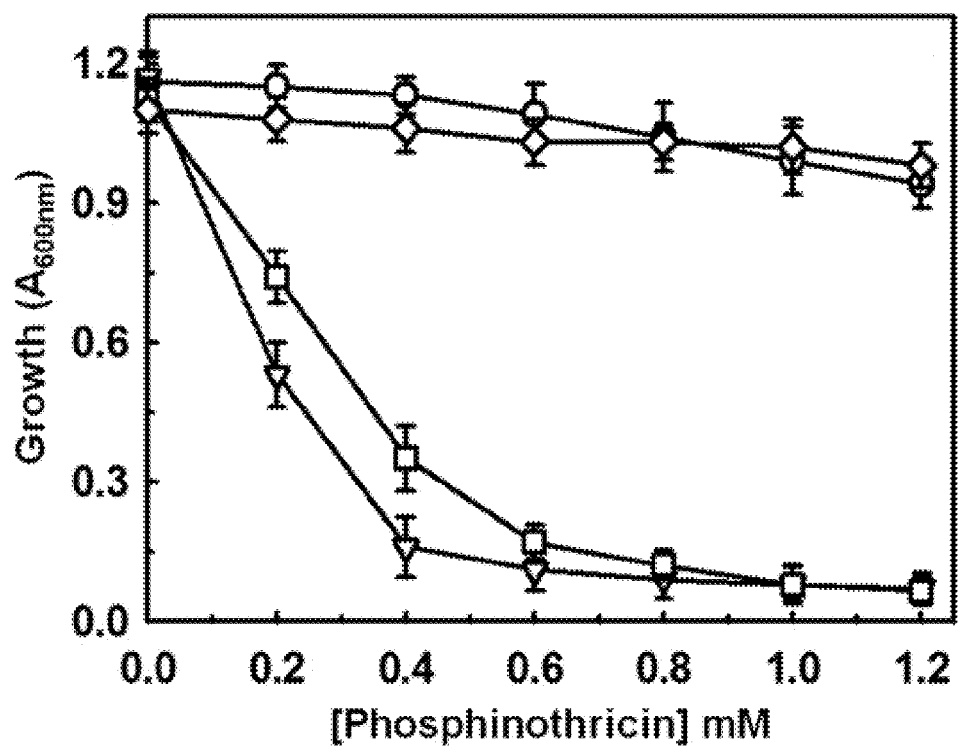
Figure 3D:
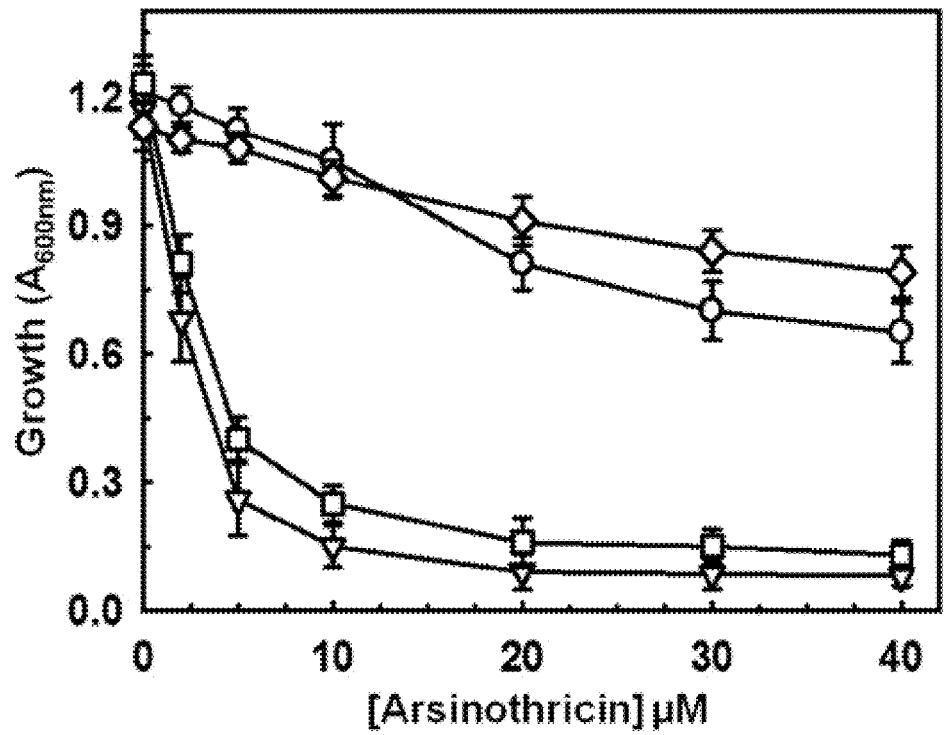

Bacterial resistance to PT is conferred by phosphinothricin N-acetyltransferases (PATs). PATs inactivate PT by acetylation of the α-amino group, which prevents binding to GS. These genes have been used to construct transgenic PT-resistant plants, allowing PT to be used for weed control. Many bacterial ars operons have genes that encode putative GCN5-related N-acetyltransferases (GNAT) (FIG. 3A). Many of these genes encode proteins closely related to phosphinothricin N-acetyltransferases (FIG. 3B). The genes are referenced herein as arsN1. The arsN1 gene of *P. putida* KT2440 (PparsN1, accession number AAN67541) was originally termed phoN1 because it confers PT resistance. The genome of *P. putida* KT2440 has two ars operons (ars1 and ars2). ars1 contains the PparsN1 gene. Wild type cells are PT resistance, while cells with a deletion of both ars operons (Δars1,2) are sensitive (FIG. 3C). Introduction of PparsN1 into *E. coli* AW3110 confers resistance.

Every characterized ars gene has been shown to have an arsenic-related function. Some ars operons contain genes of unknown function, and these genes are predicted to also have an arsenic-related function. The prevalence of arsN1 genes in multiple ars operons implies involvement in arsenic metabolism. Therefore, it is hypothesized herein that AST is a substrate of ArsN1. Parental *P. putida* is resistant to AST, while *P. putida* Δars1,2 is sensitive (FIG. 3D). *E. coli* AW3110 is similarly sensitive to AST, and heterologous expression of PparsN1 confers resistance. These results support that ArsN1 has the arsenic-related function of AST resistance. Comparing the effect of PT with AST, both *P. putida* Δars1, 2 and *E. coli* AW3110 show nearly complete inhibition by 20 μM AST, with 50% inhibition at approximately 3 μM AST. In contrast, 100 μM PT was required to give 50% inhibition. These results indicate that AST is approximately 30-fold more effective as an antibiotic compared with PT.

Example 5—PpArsN1 is an Arsinothricin-Selective N-Acetyltransferase

Crude extracts of *P. putida* expressing PparsN1 were shown to acetylate PT. Purified PpArsN1 also exhibits phosphinothricin acetyltransferase activity (Table 2). Another known GS inhibitor methionine sulfoximine (MSO) (FIG. 1D) is a poor substrate. Purified PpArsN1 has 100-fold higher affinity for AST compared with PT, and 15-fold higher catalytic efficiency ($K_{cat}/K_m$), indicating that AST is the physiological substrate of PpArsN1. The affinity and catalytic efficiency of phosphinothricin N-acetyltransferase (PAT) from *Streptomyces viridochromeogenes* (SvPAT) with AST are similar with those of PpArsN1. In contrast, SvPAT shows two orders of magnitude higher affinity for PT than PpArsN1.

TABLE 2

PpArsN1 is selective for AST among GS inhibitors

| Substrate (50 μM) | | PpArsN1 Specific activity (nmol s$^{-1}$ mg$^{-1}$) | |
|---|---|---|---|
| arsinothricin | | 49.6 ± 0.8 | |
| phosphinothricin[a] | | 13.9 ± 1.9 | |
| methionine sulfoximine | | 2.1 ± 0.1 | |

| Protein | Substrate | $K_m$ (μM) | $K_{cat}$ (s$^{-1}$) | $K_{cat}/K_m$ (M$^{-1}$ s$^{-1}$) |
|---|---|---|---|---|
| PpArsN | AST | 11 ± 3 | 1.7 ± 0.2 | 1.55 × 10$^5$ |
|  | PT[a] | 1000 ± 200 | 9.6 ± 0.9 | 0.10 × 10$^5$ |
| PAT | AST | 12 ± 2 | 2.3 ± 0.1 | 1.92 × 10$^5$ |
|  | PT[a] | 47 ± 2 | 3.1 ± 0.0 | 0.66 × 10$^5$ |

[a]Concentrations of D,L-PT were adjusted assuming only the L-enantiomer of chemically synthesized D,L-PT is a substrate.

Example 6—Crystal Structure of PpArsN1

Figure 4A:
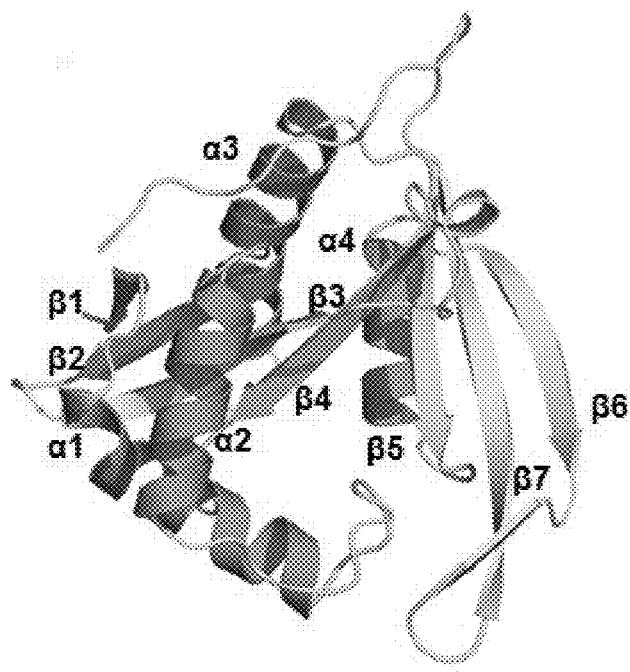
Figure 4B:
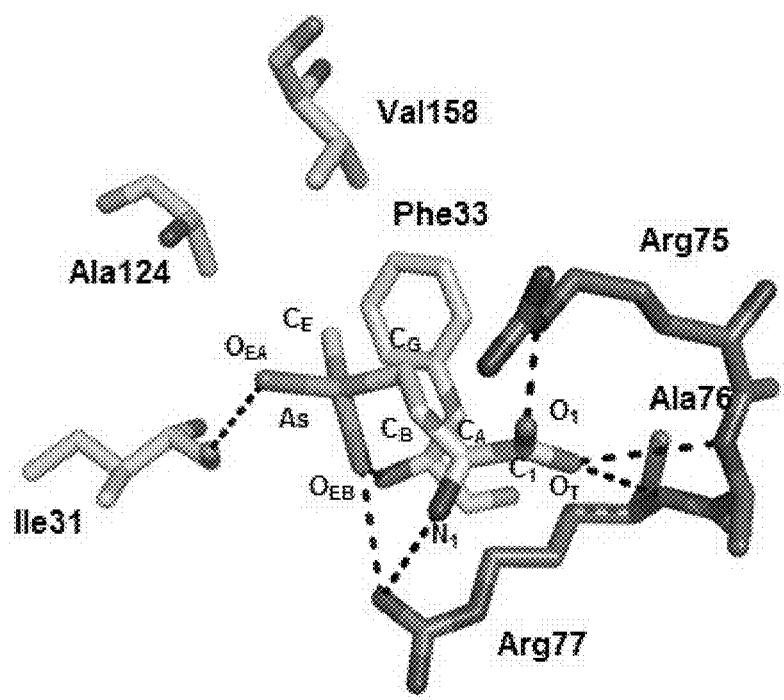
Figure 4C:
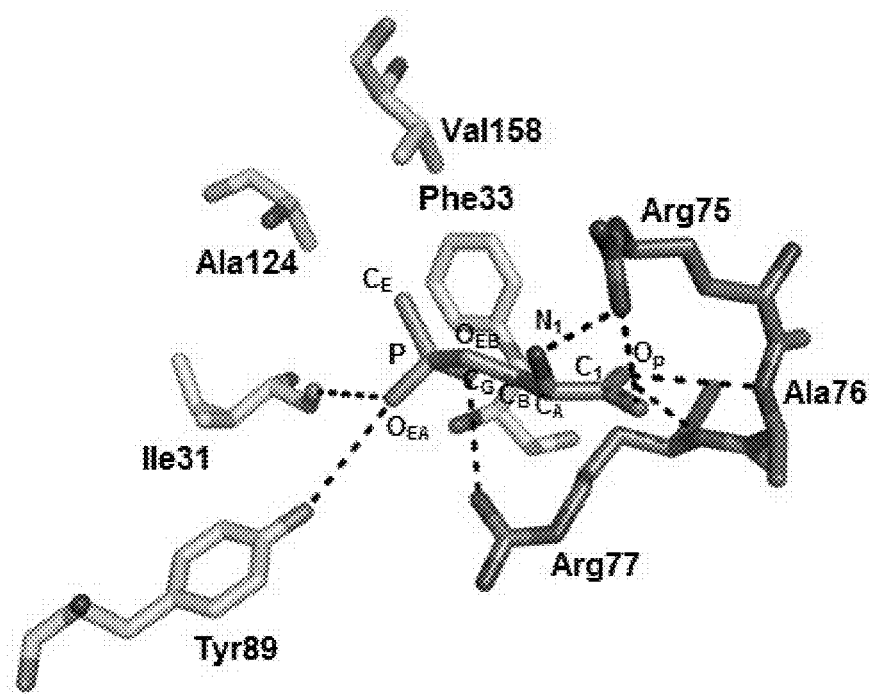
Figure 4D:
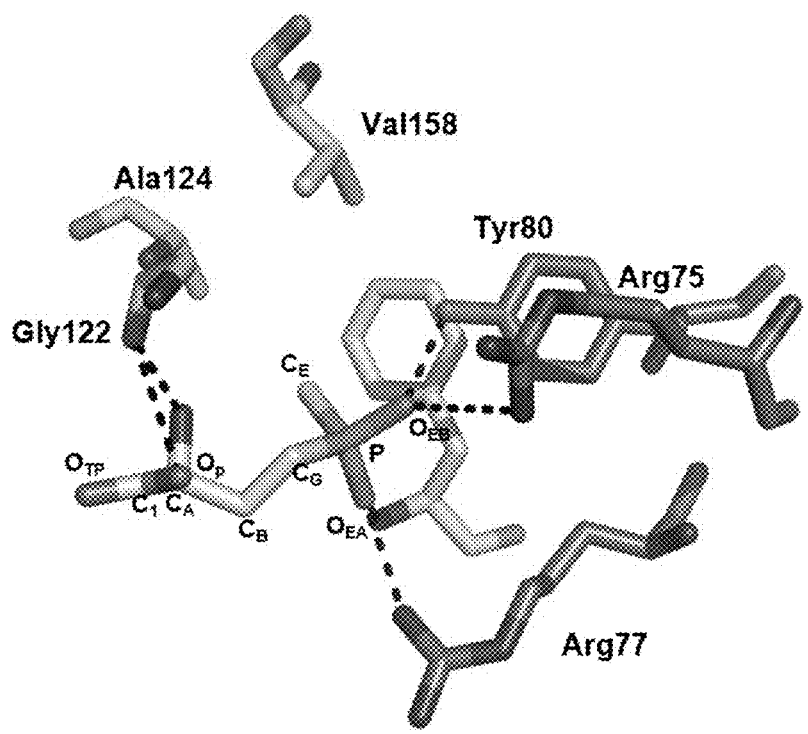
Figure 4E:
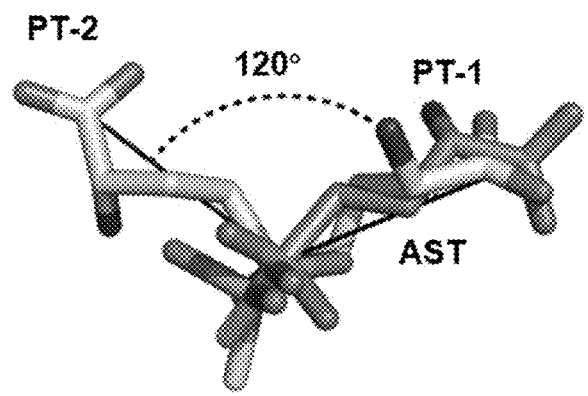
Figure 4F:
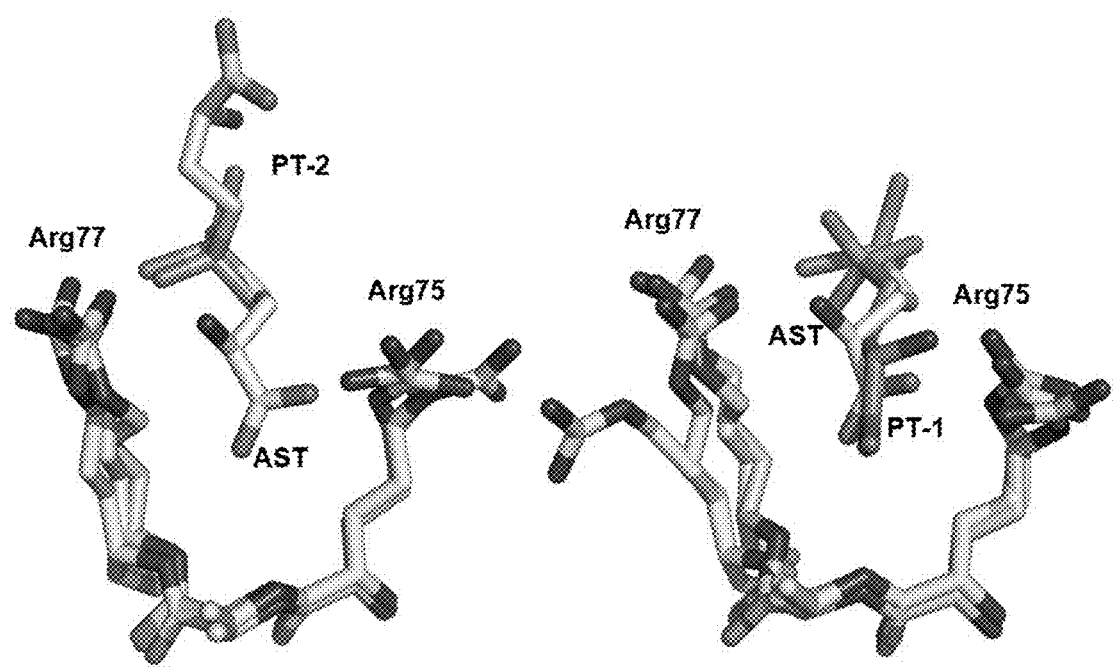

To elucidate the mechanism of PpArsN1 resistance and its selectivity for AST, the crystal structures of apo- and substrate-bound PpArsN1 were determined. The overall conformation is a three-layer α/β sandwich fold (FIG. 4A), a GNAT typical fold. PpArsN1 forms an asymmetric homodimer in solution, as shown by the extensive interactions of the subunits (FIG. 8) and size exclusion chromatography (FIG. 9), similar to other N-acetyltransferases. The AST-bound PpArsN structure confirms that AST is the L-enantiomer (FIG. 10). PpArsN1 has two AST-binding sites, which are asymmetrically formed by amino acid residues from both Chains A and B. Both active sites are composed of seven residues: four residues from one chain (Ile31, Phe33, Ala124 and Val1158) (FIG. 4B, green) and three residues from the other (Arg75, Ala76 and Arg77) (FIG. 4B, cyan). In the PT-bound structures, PT shows two confirmations. In one confirmation (PT-1) (FIG. 4C), the orientation of PT is similar to that of AST (FIG. 4B), although sets of amino acid residues used by PpArsN1 to interact with each chemical moiety in PT are slightly different from those used to interact with the corresponding chemical moiety in AST. In these structures, the predicted distance between the α-amino group of AST/PT and the sulfur atom of AcCoA is too far away to initiate the catalysis of acetylation (FIG. 11). Another conformation of PT (PT-2) (FIG. 4D) is similar to that of the PT observed in the previously reported CoA- and PT-bound ShPAT (PAT from *Streptomyces hygroscopicus*, also known as BAR). Superimposition of these two conformations of PT-bound PpArsN1 demonstrates the two different binding modes of substrates in PpArsN1 (FIG. 4E). The arsenic atom of AST closely overlaps with the phosphorus atoms in PT-1 and PT-2. The orientation of PT-1 is almost superimposable to that of AST. In contrast, the orientation of PT-2 is inclined 120° towards the AcCoA binding site with respect to those of PT-1 and AST, which brings the α-amino group of PT closer to the sulfur atom of AcCoA (FIG. 12), which is more favorable for catalysis of acetylation. Arg75 in chain A of the apo-structure also shows two conformations. One superimposes with the AST-bound PpArsN1 structure, covering the substrate-binding channel, whereas the other moves out of channel (FIG. 4F). The side chain of Arg77 in chain B also appears to cover and move away from the substrate binding site, allowing substrate access to the active site. The conformations of these two residues in the PT-bound PpArsN1, for both PT-1 and PT-2, are quite similar to those in the AST-bound PpArsN1. Arg75 and Arg77 appear to form a gate that controls substrate access.

Example 6—Use of AST for Treating Infections

Arsenic is the most ubiquitous environmental poison, and its toxicity presented a challenge to the first organisms. To adapt to high arsenic concentrations in primordial waters, microbes evolved arsenic detoxification mechanisms. In addition, microbes developed mechanisms to use arsenic for energy production. Bacteria have evolved pathways for using arsenic as an antibiotic to give them a selective growth advantage over competitors. The high selectivity of PpArsN1 for AST suggests that arsN1 genes evolved in response to the environmental challenge presented by AST producers. Phylogenetic analysis suggests that ArsN1 is the common ancestor of ArsN1, PAT (phosphinothricin (P) N-acetyltransferase) and MAT (methionine sulfoximine (MSO)N-acetyltransferase), with PAT and MAT branching off from ArsN1 (FIG. 3B), implying that the arsenical antibiotic AST is the most ancient of this class of antimicrobials. AST was identified only recently and other organo-arsenical antibiotics may exist. There are genes in ars operons for which functions have not been found; these might be resistance mechanisms against unknown arsenical natural products.

Given that the distance between the amino group of PT and the acetyl group of AcCoA is far away in the PT-1 conformation (FIG. 11) but gets closer in the PT-2 conformation (FIG. 12), it is hypothesized that the PT-2 is the conformation for the catalysis of acetylation. Then the question arises why PT binds to PpArsN1 in the PT-1 conformation, in addition to the PT-2 conformation. The α-amino group of PT needs to be deprotonated for catalysis of PT acetylation. In ShPAT, like the other GNATs, a conserved catalytic Glu88 acts as a general base, interacts with the α-amino group of PT via a water molecule and uses the water molecule as the proton shuttle to catalyze the deprotonation step. In PpArsN1, however, the Glu88 of ShPAT is replaced by Asp85 (FIG. 13). The side chain of Asp85 is not long enough to catalyze deprotonation of the α-amino group of PT in the PT-2 conformation, where no water molecule interactions were found between the α-amino group of PT and Asp85 of PpArsN1. In contrast, in the PT-1 conformation, the distance between the α-amino group of PT and Asp85 becomes closer and Asp85 coordinates with the amino group of PT via a water molecule (FIG. 13), suggesting that the substrate protonation is catalyzed by Asp85 in this conformation. A similar water molecule bridge was also observed between AST and Asp85 in AST-bound PpArsN1. Based on these results, PpArsN1 is proposed to have two separate sites for deprotonation and acetylation of the substrate (FIG. 5). In this model, PpArsN1 first captures the substrate by the deprotonation site, as seen in the PT-1 conformation (FIG. 3C), where the amino group of the substrate is deprotonated by Asp85 (FIG. 14). The deprotonated substrate is then relocated to the acetylation site, as seen in the PT-2 conformation (FIG. 3D), where the deprotonated substrate gets closer to the AcCoA (FIG. 12) and undergoes nucleophilic attach on the carbonyl bond of the acetyl group to further proceed the catalysis. A similar mechanism that uses two separate sites for deprotonation and acetylation of the substrate is proposed also for L-glutamate N-acetyltransferase from *Mycobacterium tuberculosis* based on the structural analysis. This may be a unique feature that separates PpArsN from ShPAT that utilizes one common site for both deprotonation and acetylation of the substrate (FIG. 15).

AST is more effective antibiotic than its phosphorus-containing mimetic PT because small difference in As—O and P—O bond lengths makes AST bind more tightly to GS, ArsN as well as PAT and not because of the overall greater toxicity of arsenic compared with phosphorus. Differences between arsenic and phosphorus coordination are instructive. In arsenate the As—O bond length is 1.69 Å, and, in phosphate the P—O bond length is 1.52 Å. This minute difference distorts a low-barrier H-bond and allows 4500-fold selectivity for phosphate over arsenate by the periplasmic phosphate binding protein of *Halomonas* sp. GFAJ-1. AST and PT differ from inorganic arsenate and phosphate in having C—As and C—P bonds replacing O—As and O—P bonds. In AST-bound PpArsN1, the bond lengths of As—$C_G$, As—$C_E$, As—$O_{EA}$, As—$O_{EB}$ in AST are 2.0, 1.9, 1.9 and 2.0 Å respectively. In PT, the bond lengths of P—$C_G$, P—$C_E$, P—$O_E$A and P—$O_{EB}$ in PT are 1.8, 1.8, 1.6 and 1.5 Å, respectively. Although small, these differences are critical for binding affinity. Both the arsenic atom in AST and the phosphorus atom in PT are in a tetrahedral geometry with four coordinations. The volume of the AST tetrahedron is 3.00 Å$^3$, compared with 1.86 Å$^3$ for PT. This difference can affect hydrogen bonding, hydrophobic and van der Waal contacts between the tetrahedral substrates and enzyme. This can account in part for the 100-fold higher affinity for AST compared with PT. With such knowledge a person of ordinary skill in the art can identify ArsN inhibitors that can be used in combination with AST to prevent resistance.

Example 7—Identification of Inhibitors of ArsN 1

Structure-based screening is becoming an essential tool in assisting fast and cost-effective lead discovery and optimization in early stage drug development. Certain embodiments of this invention utilize 3D structures of ArsN1 and PAT for in silico screening of virtual small molecule libraries to identify inhibitors of ArsN1. Thus, potential commercially-available ArsN1/PAT inhibitors can be identified.

In initial trials ZINC, a free database of commercially-available compounds for virtual screening was employed. Based on the structures of ArsN1 and PAT, the cavity which contains the substrate and acetyl-CoA binding sites (FIG. 16) was selected to screen effective inhibitors. AST resistant enzymes would not be able to function if these sites are blocked. The small molecules from a subset of the ZINC database of 120 million "drug-like" compounds were docked with unliganded structure of PpArsN1 and ShPAT using the open source docking program idock, which screened molecules with idock score (an in silico estimation of free energy of binding in kcal/mol units) of −10 to −14. Many compounds with the idock score within this range have been validated to bind and inhibit their target proteins. Many of the screened small molecules were predicted to cover only the acetyl-CoA site but not the substrate binding site. Those molecules were eliminated because they may inhibit other essential human N-acetyltransferases. However, some of the small molecules cover both the acetyl-CoA binding site and the AST binding site (FIG. 16). The AST and PT binding sites are unique to ArsN1/PAT, which suggests that these molecules could be specific ArsN1/PAT inhibitors. Among these commercially-available molecules, those with high affinity for both ArsN1 and PAT (Table 3) can be analyzed in vitro. Their inhibitory activity can be first examined with purified ArsN1 and PAT enzymes using AST or PT as substrates. Molecules that inhibit ArsN1/PAT in vitro can be further tested for their effect on inactivation of AST activity in cells of *E. coli* heterologously expressing either arsN or pat and in cells of intrinsically AST-resistant *P. putida* KT2440 and *Burkholderia* strains. In addition, the cytotoxic effect of these inhibitors on human HepG2 cells can be examined. The binding parameters of molecules with inhibitory activity can be assayed and the inhibitors co-crystallized with ArsN1 and PAT. These data also allow future design of more effective inhibitors.

TABLE 3

Potential ArsN1/PAT inhibitors identified by the docking analysis

| Name | ZINC ID |
|---|---|
| 2-({8-fluoro-5H-pyridazino[4,5-b]indol-4-yl}sulfanyl)-N-(1,2,3,4-tetrahydronaphthalen-1-yl)acetamide | ZINC000032752902, ZINC000032752903 |
| 3-oxo-N-({1-phenyl-1H,4H,5H,6H-cyclopenta[c]pyrazol-3-yl}methyl)-3,4-dihydro-2H-1,4-benzothiazine-6-carboxamide | ZINC000040155976 |
| 1-(4-fluorobenzoyl)-N-(3-phenyl-1H-pyrazol-4-yl)piperidine-3-carboxamide | ZINC000089847960, ZINC000089847962 |
| N-[3-({[(6-fluoro-3,4-dihydro-2H-1-benzopyran-4-yl)carbamoyl]amino}methyl)phenyl]-cyclobutanecarboxamide | ZINC000069062678, ZINC000069062685 |

TABLE 3-continued

Potential ArsN1/PAT inhibitors identified by the docking analysis

| Name | ZINC ID |
|---|---|
| 1-[1-(2-fluorobenzoyl)piperidin-4-yl]-3-[2-(3-fluoropbenyl)cyclopropyl]urea | ZINC000065507595, ZINC000067732259, ZINC000067732260, ZINC000067732262 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method of treating an infection in a subject caused by *Enterobacter cloacae* comprising administering to the subject arsinothricin or a salt thereof.

2. The method of claim 1, wherein the infection is caused by carbapenem-resistant *Enterobacter cloacae*.

3. The method of claim 1, wherein *Enterobacter cloacae* expresses phosphinothricin N-acetyltransferase and/or arsinothricin N-acetyltransferase, and the method further comprises administering to the subject an inhibitor of phosphinothricin N-acetyltransferase and arsinothricin N-acetyltransferase.

4. A method of treating an infection in a subject caused by a bacterium, the bacterium being *Enterobacter* spp. the method comprising administering to the subject arsinothricin or a salt thereof.

5. The method of claim 4, comprising administering arsinothricin or salt thereof via oral, pulmonary, buccal, suppository, intravenous, intraperitoneal, intranasal, intramuscular, or subcutaneous route.

6. The method of claim 4, wherein the bacterium is carbapenem-resistant Enterobacteriaceae, or carbapenem-resistant *Enterobacter cloacae*.

7. The method of claim 4, wherein the bacterium does not express phosphinothricin N-acetyltransferase and/or arsinothricin N-acetyltransferase.

8. The method of claim 4, wherein the bacterium expresses phosphinothricin N-acetyltransferase and/or arsinothricin N-acetyltransferase and the method further comprises administering to the subject an inhibitor of phosphinothricin N-acetyltransferase or arsinothricin N-acetyltransferase.

9. The method of claim 8, wherein the inhibitor of phosphinothricin N-acetyltransferase or arsinothricin N-acetyltransferase is:
- 2-({8-fluoro-5H-pyridazino[4,5-b]indol-4-yl}sulfanyl)-N-(1,2,3,4-tetrahydronaphthalen-1-yl)acetamide;
- 3-oxo-N-({1-phenyl-1H,4H,5H, 6H-cyclopenta[c]pyrazol-3-yl}methyl)-3,4-dihydro-2H-1,4-benzothiazine-6-carboxamide;
- 1-(4-fluorobenzoyl)-N-(3-phenyl-1H-pyrazol-4-yl)piperidine-3-carboxamide;
- N-[3-({[(6-fluoro-3,4-dihydro-2H-1-benzopyran-4-yl)carbamoyl]amino}methyl)phenyl]cyclobutanecarboxamide; or
- 1-[1-(2-fluorobenzoyl)piperidin-4-yl]-3-[2-(3-fluorophenyl)cyclopropyl]urea.

10. The method of claim 4, further comprising isolating the bacterium, testing the bacterium for the expression of phosphinothricin N-acetyltransferase and/or arsinothricin N-acetyltransferase, and administering to the subject an inhibitor of phosphinothricin N-acetyltransferase or arsinothricin N-acetyltransferase.

11. The method of claim 10, wherein the inhibitor of phosphinothricin N-acetyltransferase or arsinothricin N-acetyltransferase is:
- 2-({8-fluoro-5H-pyridazino[4,5-b]indol-4-yl}sulfanyl)-N-(1,2,3,4-tetrahydronaphthalen-1-yl)acetamide;
- 3-oxo-N-({1-phenyl-1H,4H,5H, 6H-cyclopenta[c]pyrazol-3-yl}methyl)-3,4-dihydro-2H-1,4-benzothiazine-6-carboxamide;
- 1-(4-fluorobenzoyl)-N-(3-phenyl-1H-pyrazol-4-yl)piperidine-3-carboxamide;
- N-[3-({[(6-fluoro-3,4-dihydro-2H-1-benzopyran-4-yl)carbamoyl]amino}methyl)phenyl]cyclobutanecarboxamide; or
- 1-[1-(2-fluorobenzoyl)piperidin-4-yl]-3-[2-(3-fluorophenyl)cyclopropyl]urea.

12. The method of claim 4, wherein the bacterium is carbapenem-resistant *Enterobacter cloacae*.

13. The method of claim 1, comprising administering arsinothricin or salt thereof via oral, pulmonary, buccal, suppository, intravenous, intraperitoneal, intranasal, intramuscular, or subcutaneous route.

14. The method of claim 1, wherein *Enterobacter cloacae* does not express phosphinothricin N-acetyltransferase and/or arsinothricin N-acetyltransferase.

* * * * *